US011834487B2

United States Patent
Lotem et al.

(10) Patent No.: US 11,834,487 B2
(45) Date of Patent: Dec. 5, 2023

(54) MODULATION OF SLAMF6 SPLICE VARIANTS FOR CANCER THERAPY

(71) Applicant: HADASIT MEDICAL RESEARCH SERVICES & DEVELOPMENT LTD., Jerusalem (IL)

(72) Inventors: Michal Lotem, Macabbim Reut (IL); Galit Mishan Eisenberg, Modiin (IL); Emma Hajaj, Netanya (IL)

(73) Assignee: HADASIT MEDICAL RESEARCH SERVICES & DEVELOPMENT LTD., Jerusalem (IL)

(*) Notice: Subject to any disclaimer, the term of this patent is extended or adjusted under 35 U.S.C. 154(b) by 773 days.

(21) Appl. No.: 16/968,967

(22) PCT Filed: Feb. 11, 2019

(86) PCT No.: PCT/IL2019/050163
§ 371 (c)(1),
(2) Date: Aug. 11, 2020

(87) PCT Pub. No.: WO2019/155474
PCT Pub. Date: Aug. 15, 2019

(65) Prior Publication Data
US 2021/0054043 A1    Feb. 25, 2021

Related U.S. Application Data

(60) Provisional application No. 62/629,129, filed on Feb. 12, 2018.

(51) Int. Cl.
| *A61K 35/17* | (2015.01) |
| *A61K 39/00* | (2006.01) |
| *A61P 35/00* | (2006.01) |
| *C12N 5/0783* | (2010.01) |
| *A61K 38/17* | (2006.01) |
| *C07K 14/705* | (2006.01) |

(52) U.S. Cl.
CPC . *C07K 14/70503* (2013.01); *A61K 39/001111* (2018.08); *A61P 35/00* (2018.01); *A61K 2039/5152* (2013.01); *A61K 2039/575* (2013.01); *C07K 2319/02* (2013.01)

(58) Field of Classification Search
CPC ............ A61K 35/17; A61K 2039/5156; A61K 2039/5158; A61K 39/0011
See application file for complete search history.

(56) References Cited

U.S. PATENT DOCUMENTS

| 4,376,110 A | 3/1983 | David |
| 4,816,567 A | 3/1989 | Cabilly |
| 5,225,539 A | 7/1993 | Winter |
| 5,545,807 A | 8/1996 | Surani |
| 5,693,761 A | 12/1997 | Queen |
| 5,693,762 A | 12/1997 | Queen |
| 7,592,313 B2 | 9/2009 | Zheng et al. |
| 2006/0099177 A1 | 5/2006 | June |
| 2009/0017014 A1 | 1/2009 | Valdez |
| 2009/0181009 A1 | 7/2009 | Abo et al. |
| 2010/0150886 A1 | 6/2010 | Marui |
| 2011/0171204 A1 | 7/2011 | Abo |
| 2012/0244133 A1 | 9/2012 | Rosenberg |
| 2014/0302070 A1 | 10/2014 | Chen |
| 2016/0311907 A1 | 10/2016 | Brogdon et al. |
| 2017/0334989 A1 | 11/2017 | Abo et al. |

FOREIGN PATENT DOCUMENTS

| EP | 2083088 A2 | 7/2009 |
| JP | 2005-206478 A | 8/2005 |
| JP | 2005206478 A | 8/2005 |
| WO | 8601533 A1 | 3/1986 |
| WO | 9007861 A1 | 7/1990 |
| WO | 9702671 A2 | 1/1997 |
| WO | 03008449 A1 | 1/2003 |
| WO | 2006037421 A2 | 4/2006 |
| WO | 2007045996 A1 | 4/2007 |
| WO | 2015104711 A1 | 7/2015 |
| WO | 2017019894 A1 | 2/2017 |
| WO | 2017075478 A2 | 5/2017 |
| WO | 2018020476 A1 | 2/2018 |
| WO | 2018049025 A2 | 3/2018 |
| WO | 2020261265 A1 | 12/2020 |
| WO | 2020261266 A1 | 12/2020 |

OTHER PUBLICATIONS

Bottino et al., (2001) NTB-A [correction of GNTB-A], a novel SH2D1A-associated surface molecule contributing to the inability of natural killer cells to kill Epstein-Barr virus-infected B cells in X-linked lymphoproliferative disease. J Exp Med 194(3): 235-246.
Hajaj et al., (2020) Alternative splicing of SLAMF6 in human T cells creates a co-stimulatory isoform that counteracts the inhibitory effect of the full-length receptor. bioRxiv 2020.08.21.262238; doi: https://doi.org/10.1101/2020.08.21.262238.
Hajaj et al., (2020) SLAMF6 deficiency augments tumor killing and skews toward an effector phenotype revealing it as a novel T cell checkpoint. Elife 9: e52539.
Kageyama et al., (2012) The receptor Ly108 functions as a SAP adaptor-dependent on-off switch for T cell help to B cells and NKT cell development. Immunity 36(6): 986-1002.

(Continued)

*Primary Examiner* — Barry A Chestnut
(74) *Attorney, Agent, or Firm* — RAPHAEL BELLUM PLLC

(57) ABSTRACT

The invention relates to cancer immunotherapy, particularly to improved therapeutic modalities involving specifically modulating the expression and/or activity of SLAMF6 splice variants. More specifically, embodiments of the invention provide compositions and methods for cancer therapy, including adoptive T cell transfer therapies, cell vaccines and/or polypeptide- based medicaments. In various embodiments, compositions and methods providing selective augmentation of SLAMF6 variant 3 (SLAMF6$^{var3}$) N expression or activity on T cells and/or tumor cells are provided.

25 Claims, 9 Drawing Sheets

Specification includes a Sequence Listing.

(56) References Cited

OTHER PUBLICATIONS

Yigit et al., (2019) SLAMF6 as a Regulator of Exhausted CD8+ T Cells in Cancer. Cancer Immunol Res 7(9): 1485-1496.

UniProt database entry Q96DU3; SLAF6_HUMAN. SLAM family member 6, *Homo sapiens* (Human), Gene: SLAMF6 (KALI). Retrieved from: https://www.uniprot.org/uniprotkb/Q96DU3/entry on Jul. 9, 2022. 10 pages.

Ayers et al., (2017) IFN-γ-related mRNA profile predicts clinical response to PD-1 blockade. J Clin Invest 127(8): 2930-2940.

Choo et al., (2009) A comprehensive assessment of N-terminal signal peptides prediction methods. BMC Bioinformatics 10 Suppl 15(Suppl 15): S2, pp. 1-12.

Dutta and Schwartzberg (2012) Characterization of Ly108 in the thymus: evidence for distinct properties of a novel form of Ly108. J Immunol 188(7): 3031-3041.

Hajaj et al., (2018) Diverse effects of the splice isoforms of immune receptor SLAMF6—a new regulatory mechanism. EACR-AACR-ISCR Conference: The Cutting Edge of Contemporary Cancer Research, Oct. 9-11, 2018, Jerusalem, Israel. 1 page.

Hajaj et al., (2018) SLAMF6 is a regulatory receptor for T cell activation. Cell-Weizmann Institute of Science Symposium: Next Gen Immunology. Poster Session 1 Sunday, Feb. 11, 2018; Immunity at Epithelial Barriers/Host Cell Microbe Interactions [P2.1.56]. Hadassah Hebrew University Medical Center, Israel. 1 page.

Ji et al., (2014) Identification of the genomic insertion site of Pmel-1 TCR α and β transgenes by next-generation sequencing. PLoS One 9(5): e96650; 8 pages.

Jiang et al., (2016) Role of IL-2 in cancer immunotherapy. Oncoimmunology 5(6): e1163462.

Kumar et al., (2018) A comprehensive review on the role of co-signaling receptors and Treg homeostasis in autoimmunity and tumor immunity. J Autoimmun. Author manuscript; available in PMC Dec. 1, 2019. Published in final edited form as: J Autoimmun. Dec. 2018, 95: 77-99.

Long et al., (2018) The promising immune checkpoint LAG-3: from tumor microenvironment to cancer immunotherapy. Genes Cancer 9(5-6): 176-189.

Martin and Sawyer (2019) Elucidating the structure of membrane proteins. Tech News, BioTechniques 66(4): 167-170.

Ni and Lu (2018) Interferon gamma in cancer immunotherapy. Cancer Med 7(9): 4509-4516.

Overwijk et al., (2003) Tumor regression and autoimmunity after reversal of a functionally tolerant state of self-reactive CD8+ T cells. J Exp Med 198(4): 569-580.

Rutenberg et al., (2013) NTB-A receptor potentiates anti-cancer activity of cytotoxic t lymphocytes and represents a potential druggable target for cancer immunotherapy. The Fifth Annual Meeting of the Israeli Society for Cancer Research (ISCR). The 2013 Cancer Route-Stem Cells, the Microenvironment, Gene Regulation and Novel Therapies. May 23, 2013, Ben Gurion University of the Negev, Israel. 2 pages.

Waugh et al., (2016) Molecular Profile of Tumor-Specific CD8+ T Cell Hypofunction in a Transplantable Murine Cancer Model. J Immunol 197(4): 1477-1488.

Yigit (2018) SLAMF6 is a checkpoint inhibitor of CD8+ T cell exhaustion in Chronic Lymphocytic Leukemia. SLAMF Receptors In Health and Disease: Implications for Therapeutic Targeting, 87, Dec. 31, 2018 (Dec. 31, 2018). Doctoral Thesis Utrecht University, the Netherlands. 177 pages.

NCT00612664, first posted on Jan. 30, 2008. History of Changes for study: NCT00612664; Phase II, 2nd Line Melanoma—RAND Monotherapy. Retrieved from: https://clinicaltrials.gov/ct2/history/NCT00612664?A=1&B=1&C=merged#StudyPageTop on Mar. 30, 2022. 9 pages.

Falco et al., (2004) Homophilic interaction of NTBA, a member of the CD2 molecular family: induction of cytotoxicity and cytokine release in human NK cells. Eur J Immunol 34(6): 1663-1672.

Korver et al., (2008) Potent Anti-Cancer Activity of Anti-NTB-a Monoclonal Antibodies in Preclinical Leukemia and Lymphoma Models. Blood 112 (11): 4975.

English translation of JP2005206478, pub. date: Aug. 4, 2005.

Bendig (1995) Humanization of rodent monoclonal antibodies by CDR grafting. Methods: A Companion to Methods in Enzymology 8: 83-93.

Chatterjee et al., (2011) SLAMF6-driven co-stimulation of human peripheral T cells is defective in SLE T cells. Autoimmunity 44(3): 211-8; pp. 1-14.

Colman (1994) Effects of amino acid sequence changes on antibody-antigen interactions. Res Immunol 145(1): 33-36.

Crawford et al., (2004) Chemotherapy-induced neutropenia: risks, consequences, and new directions for its management. Cancer 100(2): 228-237.

Eisenberg et al., (2014) Discovery of the immune modulatory role of SLAMF6 trough tumor-CD8-cell interactions; p. 80 [online], [retrieved on Apr. 2, 2015]. Retrieved from the Internet http://www.iscr.org.il/image/users/124131/ftp/my_files/pdf/%D7%A4%D7%95%D7%A1%D7%98%D7%A8%D7%99%D7%9D%20%D7%95%D7%AA%D7%A7%D7%A6%D7%99%D7%A8%D7%99%D7%9D%20%D7%9C%D7%90%D7%AA%D7%A8%20%D7%9E%D7%A2%D7%95%D7%93%D7%9B%D7%9F.pdf?id=16323521.

Eisenberg et al., (2018) Soluble SLAMF6 Receptor Induces Strong CD8+ T-cell Effector Function and Improves Anti-Melanoma Activity In Vivo. Cancer Immunol Res 6(2): 127-138.

Elflein et al., (2003) Rapid recovery from T lymphopenia by CD28 superagonist therapy. Blood 102(5): 1764-1770.

Hanawa et al., (2002) A novel costimulatory signaling in human T lymphocytes by a splice variant of CD28. Blood 99 (6): 2138-2145.

Keszei et al., (2011) A novel isoform of the Ly108 gene ameliorates murine lupus. J Exp Med 208(4): 811-822.

Khantasup et al., (2015) Design and Generation of Humanized Single-chain Fv Derived from Mouse Hybridoma for Potential Targeting Application. Monoclon Antib Immunodiagn Immunother 34(6): 404-417.

Korver et al., (2007) The lymphoid cell surface receptor NTB-A: a novel monoclonal antibody target for leukaemia and lymphoma therapeutics. Br J Haematol 137(4): 307-318.

Kozlovski et al., (2017) The role of RNA alternative splicing in regulating cancer metabolism. Hum Genet; DOI: 10.1007/s00439-017-1803-x. 16 pages.

Oberdoerffer et al., (2008) Regulation of CD45 alternative splicing by heterogeneous ribonucleoprotein, hnRNPLL. Science 321(5889): 686-691.

Ota et al., (2004) Complete sequencing and characterization of 21,243 full-length human cDNAs. Nat Genet 36(1): 40-45.

Rudikoff et al., (1982) Single amino acid substitution altering antigen-binding specificity. Proc Natl Acad Sci U S A 79 (6):1979-1983.

Snow et al., (2009) Restimulation-induced apoptosis of T cells is impaired in patients with X-linked lymphoproliferative disease caused by SAP deficiency. The Journal of Clinical Investigation 119(10): 2976-2989.

Snow et al., (2010) The power and the promise of restimulation-induced cell death in human immune diseases. Immunological Reviews 236(1): 68-82.

Uzana et al., (2012) Trogocytosis is a gateway to characterize functional diversity in melanoma-specific CD8+ T cell clones. The Journal of Immunology 188(2): 632-640.

Valdez et al., (2004) NTB-A, a new activating receptor in T cells that regulates autoimmune disease. Journal of Biological Chemistry 279(18): 18662-18669.

Wu et al., (2012) Adoptive T-Cell Therapy Using Autologous Tumor-Infiltrating Lymphocytes for Metastatic Melanoma: Current Status and Future Outlook. The Cancer Journal 18(2): 160-175.

Wu et al., (2016) A hematopoietic cell-driven mechanism involving SLAMF6 receptor, SAP adaptors and SHP-1 phosphatase regulates NK cell education. Nat Immunol, published online Feb. 15, 2016; doi:10.1038/ni.3369; 11 pages.

Accession No. Q96DU3, isoform 1, retrieved on Dec. 27, 2016, from https://www.ncbi.nlm.nih.gov/protein/Q96DU3.3, 11 Pages.

(56) References Cited

OTHER PUBLICATIONS

Fv Structure and Diversity in Three Dimensions. In: Fundamental Immunology, edited by Paul WE. Raven Press, New York, USA. 1993; pp. 292-295.
NCBI Reference Sequence: NM_001184714.1; *Homo sapiens* SLAM family member 6 (SLAMF6), transcript variant 1, mRNA, dated Oct. 21, 2018 (Oct. 21, 2018). Retrieved from: https://www.ncbi.nlm.nih.gov/nuccore/NM_001184714.1, on Sep. 15, 2020. 5 pages.
NCBI Reference Sequence: NM_001184715.1; *Homo sapiens* SLAM family member 6 (SLAMF6), transcript variant 3, mRNA, dated Mar. 19, 2019 (Mar. 19, 2019). Retrieved from: https://www.ncbi.nlm.nih.gov/nuccore/NM_001184715.1, on Sep. 15, 2020. 4 pages.
NCBI Reference Sequence: NM_001184716.1; *Homo sapiens* SLAM family member 6 (SLAMF6), transcript variant 4, mRNA, dated Mar. 19, 2019 (Mar. 19, 2019). Retrieved from: https://www.ncbi.nlm.nih.gov/nuccore/NM_001184716.1, on Sep. 15, 2020. 4 pages.
Predicted: SLAM family member 6 isoform X3 [Gorilla gorilla gorilla]; NCBI Reference Sequence: XP_004027766.1, REFSEQ: accession XM_004027717.2. Publication Date: Nov. 4, 2016. Retrieved from: URL: http://cancerimmunolres.aacrjournals.org/content/6/2/127.abstract, on: Apr. 16, 2019.
Hajaj et al., (2021) Alternative Splicing of the Inhibitory Immune Checkpoint Receptor SLAMF6 Generates a Dominant Positive Form, Boosting T-cell Effector Functions. Cancer Immunol Res 9(6): 637-650.
DATABASE UniProt [Online]. Sep. 23, 2008 (Sep. 23, 2008), "SubName: Full=cDNA FLJ52047, highly similar to SLAM family member 6 {ECO:0000313 | EMBL:BAG64907.1};", XP002804381. Retrieved from EBI accession No. UNIPROT:B4E1U5. Database accession No. B4E1U5, *sequence*.

SEQUENCE LISTING

<160> NUMBER OF SEQ ID NOS: 20

<210> SEQ ID NO 1
<211> LENGTH: 332
<212> TYPE: PRT
<213> ORGANISM: Homo sapiens

<400> SEQUENCE: 1

Met Leu Trp Leu Phe Gln Ser Leu Leu Phe Val Phe Cys Phe Gly Pro
1 5 10 15

```
Gly Asn Val Val Ser Gln Ser Ser Leu Thr Pro Leu Met Val Asn Gly
             20                  25                  30

Ile Leu Gly Glu Ser Val Thr Leu Pro Leu Glu Phe Pro Ala Gly Glu
         35                  40                  45

Lys Val Asn Phe Ile Thr Trp Leu Phe Asn Glu Thr Ser Leu Ala Phe
 50                  55                  60

Ile Val Pro His Glu Thr Lys Ser Pro Glu Ile His Val Thr Asn Pro
 65                  70                  75                  80

Lys Gln Gly Lys Arg Leu Asn Phe Thr Gln Ser Tyr Ser Leu Gln Leu
                 85                  90                  95

Ser Asn Leu Lys Met Glu Asp Thr Gly Ser Tyr Arg Ala Gln Ile Ser
            100                 105                 110

Thr Lys Thr Ser Ala Lys Leu Ser Ser Tyr Thr Leu Arg Ile Leu Arg
        115                 120                 125

Gln Leu Arg Asn Ile Gln Val Thr Asn His Ser Gln Leu Phe Gln Asn
    130                 135                 140

Met Thr Cys Glu Leu His Leu Thr Cys Ser Val Glu Asp Ala Asp Asp
145                 150                 155                 160

Asn Val Ser Phe Arg Trp Glu Ala Leu Gly Asn Thr Leu Ser Ser Gln
                165                 170                 175

Pro Asn Leu Thr Val Ser Trp Asp Pro Arg Ile Ser Ser Glu Gln Asp
            180                 185                 190

Tyr Thr Cys Ile Ala Glu Asn Ala Val Ser Asn Leu Ser Phe Ser Val
        195                 200                 205

Ser Ala Gln Lys Leu Cys Glu Asp Val Lys Ile Gln Tyr Thr Asp Thr
    210                 215                 220

Lys Met Ile Leu Phe Met Val Ser Gly Ile Cys Ile Val Phe Gly Phe
225                 230                 235                 240

Ile Ile Leu Leu Leu Leu Val Leu Arg Lys Arg Arg Asp Ser Leu Ser
                245                 250                 255

Leu Ser Thr Gln Arg Thr Gln Gly Pro Ala Glu Ser Ala Arg Asn Leu
            260                 265                 270

Glu Tyr Val Ser Val Ser Pro Thr Asn Asn Thr Val Tyr Ala Ser Val
        275                 280                 285

Thr His Ser Asn Arg Glu Thr Glu Ile Trp Thr Pro Arg Glu Asn Asp
    290                 295                 300

Thr Ile Thr Ile Tyr Ser Thr Ile Asn His Ser Lys Glu Ser Lys Pro
305                 310                 315                 320

Thr Phe Ser Arg Ala Thr Ala Leu Asp Asn Val Val
                325                 330

<210> SEQ ID NO 2
<211> LENGTH: 21
<212> TYPE: DNA
<213> ORGANISM: Artificial Sequence
<220> FEATURE:
<223> OTHER INFORMATION: PCR primer

<400> SEQUENCE: 2
gcggaaagca tgttgtggct g                                           21

<210> SEQ ID NO 3
<211> LENGTH: 21
<212> TYPE: DNA
<213> ORGANISM: Artificial Sequence
<220> FEATURE:
<223> OTHER INFORMATION: PCR primer
```

-continued

<400> SEQUENCE: 3
ggagacagtg aggtttggct g                                    21

<210> SEQ ID NO 4
<211> LENGTH: 20
<212> TYPE: DNA
<213> ORGANISM: Artificial Sequence
<220> FEATURE:
<223> OTHER INFORMATION: Artificial  PCR primer

<400> SEQUENCE: 4
ctgttccaat cgctcctgtt                                      20

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
ggggttaagc tgctttgtga                                      20

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
ctgttccaat cgctcctgtt                                      20

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
cagatggagc tcacaggtca                                      20

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
ctgttccaat cgctcctgtt                                      20

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
cagggagtag gactgggtga                                      20

<210> SEQ ID NO 10

```
<211> LENGTH: 25
<212> TYPE: DNA
<213> ORGANISM: Artificial Sequence
<220> FEATURE:
<223> OTHER INFORMATION: Construct 1 SgRNA Fw

<400> SEQUENCE: 10
caccgagaat cccgttcacc atcaa                                              25

<210> SEQ ID NO 11
<211> LENGTH: 24
<212> TYPE: DNA
<213> ORGANISM: Artificial Sequence
<220> FEATURE:
<223> OTHER INFORMATION: Construct 1, SgRNA Rev

<400> SEQUENCE: 11
aaacttgatg gtgaacggga ttct                                               24

<210> SEQ ID NO 12
<211> LENGTH: 28
<212> TYPE: DNA
<213> ORGANISM: Artificial Sequence
<220> FEATURE:
<223> OTHER INFORMATION: Construct 2, SgRNA Fw

<400> SEQUENCE: 12
caccgagaag acaaacagga gcgatgtt                                           28

<210> SEQ ID NO 13
<211> LENGTH: 27
<212> TYPE: DNA
<213> ORGANISM: Artificial Sequence
<220> FEATURE:
<223> OTHER INFORMATION: Construct 2, SgRNA Rev

<400> SEQUENCE: 13
aaacaacatc gctcctgttt gtcttct                                            27

<210> SEQ ID NO 14
<211> LENGTH: 161
<212> TYPE: PRT
<213> ORGANISM: Artificial Sequence
<220> FEATURE:
<223> OTHER INFORMATION: isolated ectodomain of human SLAMF6-var3

<400> SEQUENCE: 14

Val Pro His Glu Thr Lys Ser Pro Glu Ile His Val Thr Asn Pro Lys
1               5                   10                  15

Gln Gly Lys Arg Leu Asn Phe Thr Gln Ser Tyr Ser Leu Gln Leu Ser
            20                  25                  30

Asn Leu Lys Met Glu Asp Thr Gly Ser Tyr Arg Ala Gln Ile Ser Thr
        35                  40                  45

Lys Thr Ser Ala Lys Leu Ser Ser Tyr Thr Leu Arg Ile Leu Arg Gln
    50                  55                  60

Leu Arg Asn Ile Gln Val Thr Asn His Ser Gln Leu Phe Gln Asn Met
65                  70                  75                  80

Thr Cys Glu Leu His Leu Thr Cys Ser Val Glu Asp Ala Asp Asp Asn
                85                  90                  95

Val Ser Phe Arg Trp Glu Ala Leu Gly Asn Thr Leu Ser Ser Gln Pro
            100                 105                 110

Asn Leu Thr Val Ser Trp Asp Pro Arg Ile Ser Ser Glu Gln Asp Tyr
        115                 120                 125
```

-continued

```
Thr Cys Ile Ala Glu Asn Ala Val Ser Asn Leu Ser Phe Ser Val Ser
    130                 135                 140

Ala Gln Lys Leu Cys Glu Asp Val Lys Ile Gln Tyr Thr Asp Thr Lys
145                 150                 155                 160

Met

<210> SEQ ID NO 15
<211> LENGTH: 190
<212> TYPE: PRT
<213> ORGANISM: Artificial Sequence
<220> FEATURE:
<223> OTHER INFORMATION: Chimeric ectodomain precursor

<400> SEQUENCE: 15

Met Leu Trp Leu Phe Gln Ser Leu Leu Phe Val Phe Cys Phe Gly Pro
1               5                   10                  15

Gly Asn Val Val Ser Val Pro His Glu Thr Lys Ser Pro Glu Ile His
            20                  25                  30

Val Thr Asn Pro Lys Gln Gly Lys Arg Leu Asn Phe Thr Gln Ser Tyr
        35                  40                  45

Ser Leu Gln Leu Ser Asn Leu Lys Met Glu Asp Thr Gly Ser Tyr Arg
    50                  55                  60

Ala Gln Ile Ser Thr Lys Thr Ser Ala Lys Leu Ser Ser Tyr Thr Leu
65                  70                  75                  80

Arg Ile Leu Arg Gln Leu Arg Asn Ile Gln Val Thr Asn His Ser Gln
                85                  90                  95

Leu Phe Gln Asn Met Thr Cys Glu Leu His Leu Thr Cys Ser Val Glu
            100                 105                 110

Asp Ala Asp Asn Val Ser Phe Arg Trp Glu Ala Leu Gly Asn Thr
        115                 120                 125

Leu Ser Ser Gln Pro Asn Leu Thr Val Ser Trp Asp Pro Arg Ile Ser
    130                 135                 140

Ser Glu Gln Asp Tyr Thr Cys Ile Ala Glu Asn Ala Val Ser Asn Leu
145                 150                 155                 160

Ser Phe Ser Val Ser Ala Gln Lys Leu Cys Glu Asp Val Lys Ile Gln
                165                 170                 175

Tyr Thr Asp Thr Lys Met Gly Ser His His His His His
            180                 185                 190

<210> SEQ ID NO 16
<211> LENGTH: 281
<212> TYPE: PRT
<213> ORGANISM: Homo sapiens

<400> SEQUENCE: 16

Met Leu Trp Leu Phe Gln Ser Leu Leu Phe Val Phe Cys Phe Gly Pro
1               5                   10                  15

Val Pro His Glu Thr Lys Ser Pro Glu Ile His Val Thr Asn Pro Lys
            20                  25                  30

Gln Gly Lys Arg Leu Asn Phe Thr Gln Ser Tyr Ser Leu Gln Leu Ser
        35                  40                  45

Asn Leu Lys Met Glu Asp Thr Gly Ser Tyr Arg Ala Gln Ile Ser Thr
    50                  55                  60

Lys Thr Ser Ala Lys Leu Ser Ser Tyr Thr Leu Arg Ile Leu Arg Gln
65                  70                  75                  80

Leu Arg Asn Ile Gln Val Thr Asn His Ser Gln Leu Phe Gln Asn Met
```

```
                         85                   90                   95
Thr Cys Glu Leu His Leu Thr Cys Ser Val Glu Asp Ala Asp Asn
                100                 105                 110

Val Ser Phe Arg Trp Glu Ala Leu Gly Asn Thr Leu Ser Ser Gln Pro
            115                 120                 125

Asn Leu Thr Val Ser Trp Asp Pro Arg Ile Ser Ser Glu Gln Asp Tyr
        130                 135                 140

Thr Cys Ile Ala Glu Asn Ala Val Ser Asn Leu Ser Phe Ser Val Ser
145                 150                 155                 160

Ala Gln Lys Leu Cys Glu Asp Val Lys Ile Gln Tyr Thr Asp Thr Lys
                165                 170                 175

Met Ile Leu Phe Met Val Ser Gly Ile Cys Ile Val Phe Gly Phe Ile
            180                 185                 190

Ile Leu Leu Leu Leu Val Leu Arg Lys Arg Arg Asp Ser Leu Ser Leu
        195                 200                 205

Ser Thr Gln Arg Thr Gln Gly Pro Glu Ser Ala Arg Asn Leu Glu Tyr
    210                 215                 220

Val Ser Val Ser Pro Thr Asn Asn Thr Val Tyr Ala Ser Val Thr His
225                 230                 235                 240

Ser Asn Arg Glu Thr Glu Ile Trp Thr Pro Arg Glu Asn Asp Thr Ile
                245                 250                 255

Thr Ile Tyr Ser Thr Ile Asn His Ser Lys Glu Ser Lys Pro Thr Phe
            260                 265                 270

Ser Arg Ala Thr Ala Leu Asp Asn Val
        275                 280

<210> SEQ ID NO 17
<211> LENGTH: 221
<212> TYPE: PRT
<213> ORGANISM: Homo sapiens

<400> SEQUENCE: 17

Met Leu Trp Leu Phe Gln Ser Leu Leu Phe Val Cys Phe Gly Pro
1               5                   10                  15

Gly Gln Leu Arg Asn Ile Gln Val Thr Asn His Ser Gln Leu Phe Gln
            20                  25                  30

Asn Met Thr Cys Glu Leu His Leu Thr Cys Ser Val Glu Asp Ala Asp
        35                  40                  45

Asp Asn Val Ser Phe Arg Trp Glu Ala Leu Gly Asn Thr Leu Ser Ser
    50                  55                  60

Gln Pro Asn Leu Thr Val Ser Trp Asp Pro Arg Ile Ser Ser Glu Gln
65                  70                  75                  80

Asp Tyr Thr Cys Ile Ala Glu Asn Ala Val Ser Asn Leu Ser Phe Ser
                85                  90                  95

Val Ser Ala Gln Lys Leu Cys Glu Asp Val Lys Ile Gln Tyr Thr Asp
            100                 105                 110

Thr Lys Met Ile Leu Phe Met Val Ser Gly Ile Cys Ile Val Phe Gly
        115                 120                 125

Phe Ile Ile Leu Leu Leu Leu Val Leu Arg Lys Arg Arg Asp Ser Leu
    130                 135                 140

Ser Leu Ser Thr Gln Arg Thr Gln Gly Pro Ala Glu Ser Ala Arg Asn
145                 150                 155                 160

Leu Glu Tyr Val Ser Val Ser Pro Thr Asn Asn Thr Val Tyr Ala Ser
                165                 170                 175
```

Val Thr His Ser Asn Arg Glu Thr Glu Ile Trp Thr Pro Arg Glu Asn
            180                 185                 190

Asp Thr Ile Thr Ile Tyr Ser Thr Ile Asn His Ser Lys Glu Ser Lys
            195                 200                 205

Pro Thr Phe Ser Arg Ala Thr Ala Leu Asp Asn Val Val
    210                 215                 220

<210> SEQ ID NO 18
<211> LENGTH: 156
<212> TYPE: PRT
<213> ORGANISM: Artificial Sequence
<220> FEATURE:
<223> OTHER INFORMATION: isolated ectodomain of human SLAMF6-var3

<400> SEQUENCE: 18

Lys Ser Pro Glu Ile His Val Thr Asn Pro Lys Gln Gly Lys Arg Leu
1               5                   10                  15

Asn Phe Thr Gln Ser Tyr Ser Leu Gln Leu Ser Asn Leu Lys Met Glu
            20                  25                  30

Asp Thr Gly Ser Tyr Arg Ala Gln Ile Ser Thr Lys Thr Ser Ala Lys
        35                  40                  45

Leu Ser Ser Tyr Thr Leu Arg Ile Leu Arg Gln Leu Arg Asn Ile Gln
    50                  55                  60

Val Thr Asn His Ser Gln Leu Phe Gln Asn Met Thr Cys Glu Leu His
65                  70                  75                  80

Leu Thr Cys Ser Val Glu Asp Ala Asp Asp Asn Val Ser Phe Arg Trp
                85                  90                  95

Glu Ala Leu Gly Asn Thr Leu Ser Ser Gln Pro Asn Leu Thr Val Ser
            100                 105                 110

Trp Asp Pro Arg Ile Ser Ser Glu Gln Asp Tyr Thr Cys Ile Ala Glu
        115                 120                 125

Asn Ala Val Ser Asn Leu Ser Phe Ser Val Ser Ala Gln Lys Leu Cys
    130                 135                 140

Glu Asp Val Lys Ile Gln Tyr Thr Asp Thr Lys Met
145                 150                 155

<210> SEQ ID NO 19
<211> LENGTH: 573
<212> TYPE: DNA
<213> ORGANISM: Artificial Sequence
<220> FEATURE:
<223> OTHER INFORMATION: Polynucleotide encoding chimeric ectodomain
      precursor

<400> SEQUENCE: 19
atgttgtggc tgttccaatc gctcctgttt gtcttctgct ttggcccagg gaatgtagtt      60
tcagtacccc atgaaaccaa aagtccagaa atccacgtga ctaatccgaa acagggaaag     120
cgactgaact tcacccagtc ctactcccctg caactcagca acctgaagat ggaagacaca    180
ggctcttaca gagcccagat atccacaaag acctctgcaa agctgtccag ttacactctg     240
aggatattaa gacaactgag gaacatacaa gttaccaatc acagtcagct atttcagaat     300
atgacctgtg agctccatct gacttgctct gtggaggatg cagatgacaa tgtctcattc     360
agatgggagg ccttgggaaa cacactttca gtcagccaa acctcactgt ctcctgggac      420
cccaggattt ccagtgaaca ggactacacc tgcatagcag agaatgctgt cagtaattta     480
tccttctctg tctctgccca gaagctttgc gaagatgtta aaattcaata tacagatacc     540
aaaatgggat ctcaccacca ccaccaccac tga                                  573

```
<210> SEQ ID NO 20
<211> LENGTH: 5
<212> TYPE: PRT
<213> ORGANISM: Artificial Sequence
<220> FEATURE:
<223> OTHER INFORMATION: synthetic peptide

<400> SEQUENCE: 20

Gly Asn Val Val Ser
1               5
```

MODULATION OF SLAMF6 SPLICE VARIANTS FOR CANCER THERAPY

FIELD OF THE INVENTION

The invention relates to cancer immunotherapy, particularly to improved therapeutic modalities involving the differential modulation of expression and/or activity of SLAMF6 splice variants.

BACKGROUND OF THE INVENTION

The SLAM (signaling lymphocytic activation molecules) family of receptors is typical of the homotypic-binding molecules involved in immune modulation, which are expressed on cells of hematopoietic origin. SLAM family proteins are members of the CD2 subgroup of the immunoglobulin (Ig) superfamily. SLAM family member 6 (SLAMF6), also known as NK-T-B antigen (NTB-A), CD352, Ly-108, SF2000 and KALI, is a type I transmembrane protein, expressed on natural killer (NK), T and B cells. SLAMF6 exhibits homotypic interactions mediated by recruitment of SLAM associated protein (SAP) and additional adapter proteins to the receptor complex The human SLAMF6 gene is transcribed into an 8-exon mRNA encoding for the SLAMF6 polypeptide. However, the existence of additional SLAMF6 isoforms (Ota et al, Nature Genetics 36, 40-45 (2004), characterized by certain in-frame sequence deletions, has been suggested. Unless indicated otherwise, and unless accompanied by identification of a particular isoform, the terms "SLAMF6" and "NTB-A" as used herein refer to canonical SLAMF6 (also referred to herein as SLAMF6 isoform 1, variant 1 or SLAMF6$^{var1}$).

SLAMF6 contains two extracellular Ig-like domains and three cytoplasmic tyrosine-based signaling motifs, one of which is included in a classical immunoreceptor tyrosine-based inhibitory motif. Engagement of SLAMF6 on human T cells can substitute the CD28 co-stimulatory pathway and induce polarization toward a Th1 phenotype. However, CD4-positive T cells from Ly-108 knockout mice (the murine SLAMF6 ortholog) show impairment in IL-4 production, suggesting a role of SLAMF6 in Th2 polarization. The reason for this discrepancy is not fully elucidated. Activation of SLAMF6 on human NK cells stimulates cytotoxicity and proliferation, as well as IFN-γ and TNF-α production.

Valdez et al (J Biol Chem 2004, 279(18), pp. 18662-18669 teach that SLAMF6 activates T cells by homotypic interactions, and specifically enhances Th1 properties. An NTB-A-Fc fusion protein, produced by fusing the first 226 amino acids of NTB-A to the Fc portion of murine IgG1, was found to inhibit B cell isotype switching, commonly induced by Th1-type cytokines, and inhibited a Th1-dependent autoimmune disease (EAE model). Thus, the reported NTB-A fusion protein was found to act as an SLAMF6 antagonist in the experimental systems reported by Valdez et al.

US 2009/017014 to Valdez et al is directed to the PRO20080 polypeptide (having an amino acid sequence corresponding to that of canonical SLAMF6), the extracellular portion thereof, homologs, agonists and antagonists thereof, which are suggested as putative modulators of immune diseases. The '014 publication suggests the use of certain immunostimulating compounds disclosed therein in immunoadjuvant therapy for the treatment of cancer.

Uzana et al. (J Immunol 2012, 188, pp. 632-640) disclose that SLAMF6 blockade on antigen presenting cells (APC) by specific antibodies inhibited cytokine secretion from CD8$^+$ lymphocytes. While the publication suggests canonical SLAMF6 as a potential target for improving anti-cancer immunotherapy, experimental exploration of the relevance of this approach is said to be warranted, since similar approaches, targeting other co-stimulatory receptors such as CD28 with agonistic antibodies, ended up in a fatal outcome in clinical trials.

Since SLAMF6 is expressed on certain hematopoietic tumors, vaccination using peptide epitopes derived from this molecule has been proposed, to induce an anti-tumor immune response against tumors aberrantly expressing this antigen. For example, WO 2006/037421 discloses 338 peptide sequences derived from HLA class II molecules of human tumor cell lines, which can be used in vaccine compositions for eliciting anti-tumor immune responses. Among these sequences is a 16 amino acid peptide corresponding to positions 103-118 of SLAMF6. In addition, targeting these epitopes with antibodies or immunotoxin conjugates thereof has been suggested. For instance, US2011171204 discloses anti-NTB-A antibodies and antigen-binding fragments thereof, and methods of using the same to bind NTB-A and treat diseases, such as hematologic malignancies, which are characterized by expression of NTB-A. Additional antibodies against NTB-A are described, for example, by Krover et al. (British Journal of Haematology 2007, 137, pp. 307-318). These antibodies exerted cytotoxic effects on NTB-A expressing lymphocytes, and had no effect on T cell proliferation or cytokine secretion.

EP2083088 discloses a method for treating cancer in a patient comprising modulating the level of an expression product of a gene selected from the group consisting of inter alia SLAMF6, wherein the cancer is selected from the group consisting of melanoma, breast cancer, colon cancer, kidney cancer, liver cancer, lung cancer, ovary cancer, pancreatic cancer, prostate cancer, uterine cancer, cervical cancer, bladder cancer, stomach cancer or skin cancer. The publication discloses that the method is useful for treating a patient characterized by over-expression of said gene.

WO 03/008449 relates to NTB-A polypeptides, nucleic acid molecules encoding the same and uses thereof. The publication also relates to methods of regulating NK cells activity by regulating the activity of NTB-A in vitro, ex vivo or in vivo, and to methods of screening active compounds using NTB-A or fragments thereof, or nucleic acid encoding the same, or recombinant host cells expressing said polypeptide. Further disclosed is the use of a compound that regulates the activity of a NTB-A polypeptide in the preparation of a medicament to regulate an immune function in a subject.

Snow et al. (J. Clin. Invest. 2009, 119, pp. 2976-2989; Immunol Rev. 2010, 236, pp. 68-82) examined the role of NTB-A and its downstream effector SAP, in the regulation of restimulation-induced cell death (RICD) of T cells obtained from healthy donors and patients with X-linked lymphoproliferative disease (XLP, a rare congenital immunodeficiency). The publications report that in normal donor T cells, NTB-A is positively involved in, and necessary for, TCR-induced apoptosis. In contrast, in XLP patients this phenomenon is reversed, as NTB-A was found to contribute to RICD resistance in XLP T cells.

WO 2015/104711, to some of the present inventors, discloses the use of soluble NTB-A polypeptides or agonists thereof for the treatment of cancer patients, for preventing and treating cytopenia in susceptible patients, and for the ex vivo preparation of improved T cell compositions for adoptive cell therapy. Specifically, WO '711 discloses administration of an isolated NTB-A ectodomain or an agonist thereof to a subject, or incubation of T cells with an isolated NTB-A ectodomain or an agonist thereof, in particular in the treatment of tumors characterized by lack of substantial NTB-A surface expression, solid tumors and tumors characterized by surface expression of CD137. The sequence of NTB-A as disclosed in the Examples of WO '711 corresponds to that of canonical human SLAMF6.

Eisenberg et al. (Cancer Immunol Res; 6(2) 2018), of some of the present inventors, further describes experiments performed using a 203-amino acid sequence of the canonical human SLAMF6 ectodomain (fused with a polyhistidine tag at the C-terminus, Novoprotein) on CD8+ T-cell effector function and anti-melanoma activity.

Due to the various biological effects of SLAMF6 as identified in different cells and different clinical or experimental settings, it has been characterized as a dual receptor, capable of exerting either activating or inhibitory effects in the context of immune modulation. While not fully elucidated, the direction of the response has been attributed to the intracellular tyrosine switch motifs (ITSM) of SLAMF6, based on experiments in mouse models (Keszei et al., J. Exp. Med. 2011, 208(4): 811-822).

Much information has accumulated regarding the contribution of unbalanced alternative splicing to cancer development, and the formation of pro-tumorigenic isoforms (Kozlovski, I., et al., Hum Genet, 2017, 136(9): p. 1113-1127). Alternative splicing is not unique to cancer, and over 90% of genes undergo this process. Immune receptors are no exception, and the best-recognized example is the transmembrane protein CD45, whose spliced isoforms distinguish naive from activated T cells (Oberdoerffer, S., et al., Science, 2008, 321(5889): p. 686-91). As for other immune modulatory receptors, omission of exon 2, encoding their Ig variable domain, is common to all IgSF receptors. Surprisingly, the functional consequences are largely unknown. A single study showed that a CD28 isoform missing the second exon enhanced CD28-mediated signaling, due to noncovalent association with canonical CD28, and acted as a signal amplifier (Hanawa, H., et al., Blood, 2002, 99(6): p. 2138-45). With the disastrous record of anti-CD28 treatment, this observation was not taken further.

US 2014/0302070 relates to an isoform of human PD1 (Δ42PD1) that contains a 42-nucleotide in-frame deletion located at an exon 2 domain. US '070 discloses that this isoform does not engage PD-L1/PD-L2 and can induce the production of pro-inflammatory cytokines, and suggests its use as an intramolecular adjuvant to develop a fusion DNA vaccine for enhancing antigen-specific CD8+ T cell immunity, and for prevention of pathogenic infection and/or cancer. US '070 further suggests the use of soluble Δ42PD1 protein or neutralizing antibodies as a therapeutic target for autoimmune diseases.

Isoforms of murine SLAMF6 (Ly-108) have been reported and characterized (Keszei et al., 2011 ibid, Wu et al., Nat Immunol. 2016, Apr; 17(4):387-96). The three identified Ly-108 isoforms, resulting from alternative splicing, have identical extracellular domains but differing cytoplasmic tails, due to omission of one or more of exons 7-9 (encoding inter alia for the ITSM motifs). Ly-108 isoforms were found to be associated with either susceptibility to, or protection from, lupus-related autoimmunity in mice. However, no difference in the activity of Ly-108 isoforms was found in the context of anti-tumor immunity. Rather, Wu et al. have reported that expression of different Ly-108 isoforms in NK cells resulted in enhanced responsiveness towards non-hematopoietic tumor cell lines, regardless of the transfected isoform. Wu et al. have also reported that SLAMF6 knockout by genome editing of human NK cells resulted in decreased anti-cancer activity.

No equivalent isoforms with altered cytoplasmic tails (as detected and characterized in mice) were identified in human SLAMF6. Rather, SLAMF6 variant 2 (SLAMF6$^{var2}$) differs from canonical SLAMF6 (SLAMF6$^{var1}$) by deletion of a single alanine at position 266 (corresponding to the cytoplasmic tail), SLAMF6 variant 3 (SLAMF6$^{var3}$) lacks amino acids (aa) 17-65 of exon 2 (corresponding to the extracellular domain), and SLAMF6 variant 4 (SLAMF6$^{var4}$) lacks a larger portion of exon 2, encoding aa 17-128. The biological and clinical significance of any purported alternatively spliced variants in human SLAMF6 has not been hitherto described or determined.

Advances in cancer immunotherapy reportedly exhibited a major effect on expanding patient survival. Yet, partial efficacy of these treatments, including those based on CTLA-4 or PD-1 targeting, indicate the need to find additional solutions to overcome barriers that prevent effective anti-cancer immune responses. There is an unmet need for the development of compositions and methods for immunotherapy with enhanced efficacy and/or safety.

SUMMARY OF THE INVENTION

The invention relates to cancer immunotherapy, particularly to improved therapeutic modalities involving the modulation of expression and/or activity of SLAMF6 splice variants. More specifically, embodiments of the invention provide compositions and methods for cancer therapy of human subjects, including adoptive T cell transfer therapies, cell vaccines and/or polypeptide-based medicaments.

The invention is based, in part, on the surprising discovery that various SLAMF6 isoforms are concomitantly expressed in resting and activated T cells, and manifest distinct and even opposing biological effects in the context of anti-tumor immunity. Specifically, it is now disclosed for the first time that a splice variant of human SLAMF6, which lacks a part of exon 2 that encodes a sequence of the extracellular domain, namely SLAMF6 variant 3 (SLAMF6$^{var3}$), exerts a strong agonistic effect on T cell activity and anti-tumor immunity. In contradistinction, other SLAMF6 variants, including canonical human SLAMF6 (variant 1, SLAMF6$^{var1}$), and a splice variant lacking a larger portion of exon 2 (variant 4, SLAMF6$^{var4}$), either exerted significantly weaker agonistic effects, or even mediated down-regulating effects, resulting in reduced anti-tumor immunity. The invention is further based, in part, on the development of therapeutic compositions manifesting outstanding anti-cancer activity comprising an isolated human SLAMF6$^{var3}$ ectodomain, as described herein.

According to various embodiments, the compositions and methods of the invention are useful for providing a SLAMF6 variant 3 (SLAMF6$^{var3}$)-directed T cell stimulation to the subject to be treated (providing activation mediated by, or through, engagement or administration of SLAMF6$^{var3}$ or an ectodomain thereof). In some embodiments, a SLAMF6$^{var3}$-direcetd stimulation may be provided e.g. by administering to said subject an isolated SLAMF6$^{var3}$ ectodomain, a T-cell composition manipulated ex vivo to augment SLAMF6$^{var3}$-directed T cell stimulation, and/or a cell vaccine engineered to express selectively or preferentially SLAMF6$^{var3}$, as will be described in further detail below. In some embodiments, providing a SLAMF6$^{var3}$-directed T cell stimulation comprises selectively or preferentially inhibiting or down-regulating the expression and/or activity of canonical SLAMF6 (variant 1, SLAMF6$^{var1}$) as will be described in further detail below.

In one aspect, the invention provides a therapeutic cell composition comprising a cell population engineered to express preferentially SLAMF6$^{var3}$.

As used herein, preferential (or differential) expression refers to the relative level of expression compared to the respective expression level prior to manipulation. With respect to SLAMF6$^{var3}$, this term further refers to its relative expression level compared to other SLAMF6 variants, and in particular SLAMF6$^{var1}$. Accordingly, in one embodiment, cells (e.g. T cells) expressing preferentially SLAMF6$^{var3}$ have been engineered (or otherwise manipulated) to selectively up-regulate SLAMF6$^{var3}$ expression. For example, without limitation, the cells (e.g. T cells) may be transfected or transduced with a nucleic acid construct encoding for SLAMF6$^{var3}$, regulated by a strong or inducible promoter. In another embodiment, said ells (e.g. T cells) have been engineered to selectively down-regulate SLAMF6$^{var1}$ expression. In various embodiments, suitable methods for down-regulating SLAMF6$^{var1}$ expression may include the use of nucleic acid agents including but not limited to antisense, RNA interference molecules (e.g. siRNA), gene editing constructs (e.g. CRISPR-Cas9 based constructs) and the like. It is to be understood, that suitable agents for use according to these methods are directed to regions that are unique to SLAMF6$^{var1}$ such that its expression is reduced selectively, i.e. without concomitantly reducing SLAMF6$^{var3}$ expression.

In various embodiments, the therapeutic cell composition comprising a cell population engineered to express preferentially SLAMF6$^{var3}$ is selected from the group consisting of: an adoptive transfer T cell composition, a tumor cell vaccine and a dendritic cell (DC) vaccine. In one embodiment the cell population is a human T cell population and the composition is an adoptive transfer T cell composition. In another embodiment the cell population is a human tumor cell population and the cell vaccine is a tumor cell vaccine. In a particular embodiment said tumor cell population is a melanoma cell population. In yet another embodiment the cell population is a human DC population and the cell vaccine is a DC vaccine. In another embodiment the cell population has been engineered to selectively up-regulate SLAMF6$^{var3}$ expression. In another embodiment, the cell population has been engineered to selectively down-regulate SLAMF6$^{var1}$ expression. In yet another embodiment, the cell population has been engineered to selectively up-regulate SLAMF6$^{var3}$ expression and to selectively down-regulate SLAMF6$^{var1}$ expression. In another embodiment the cell population has been engineered to express SLAMF6$^{var3}$ exogenously.

In another aspect, there is provided a therapeutic cell composition comprising a cell population engineered to express preferentially SLAMF6$^{var3}$ as described herein, for use in treating cancer in a human subject in need thereof In one embodiment the cell population is a human T cell population and said composition is an adoptive transfer T cell composition, and said T cells are autologous, or are allogeneic T cells histocompatible with said subject. In another embodiment said T cells have been generated by a method comprising modulating ex vivo T cells of the subject, or of a donor histocompatible with said subject, to express preferentially SLAMF6$^{var3}$, and formulating the resulting T cells as an adoptive transfer composition for cancer treatment. In another embodiment said T cells have been further expanded and/or activated by incubation with an isolated SLAMF6$^{var3}$ ectodomain. In another embodiment the cell population is a human tumor cell population and the cell vaccine is a tumor cell vaccine. In another embodiment the tumor cell population is a melanoma cell population. In another embodiment the cell population is a DC population and the cell vaccine is a DC vaccine.

In another aspect there is provided a method for treating cancer in a human subject in need thereof, comprising administering to the subject T cells engineered to express preferentially SLAMF6$^{var3}$. In one embodiment, the T cells have been engineered to selectively up-regulate SLAMF6$^{var3}$ expression. In another embodiment, the T cells have been engineered to selectively down-regulate SLAMF6$^{var1}$ expression. In yet another embodiment, the T cells have been engineered to selectively up-regulate SLAMF6$^{var3}$ expression and to selectively down-regulate SLAMF6$^{var1}$ expression. In another embodiment said T cells are autologous. In another embodiment said T cells are allogeneic T cells histocompatible with said subject.

In another embodiment, the method comprises:
a) obtaining T cells form the subject, or from a donor histocompatible with the subject;
b) modulating the cells ex vivo to express preferentially SLAMF6$^{var3}$; and
c) adoptively transferring the resulting T cells to said subject to thereby treat cancer in said subject.

In another embodiment, the T cells are further expanded and/or activated by incubation with an isolated SLAMF6$^{var3}$ ectodomain prior to administration to said subject.

In another aspect there is provided a method for treating cancer in a human subject in need thereof, comprising administering to said subject a cell vaccine comprising a cell population engineered to express preferentially SLAMF6$^{var3}$. In one embodiment, the cell population is a tumor cell population, and the cell vaccine is a tumor cell vaccine. In a particular embodiment the tumor cell population is a melanoma cell population. In another embodiment the cell population is a dendritic cell (DC) and the cell vaccine is a DC vaccine. In another embodiment the cell population has been engineered to selectively up-regulate SLAMF6$^{var3}$ expression. In another embodiment, the cell population has been engineered to selectively down-regulate SLAMF6$^{var1}$ expression. In yet another embodiment, the cell population has been engineered to selectively up-regulate SLAMF6$^{var3}$ expression and to selectively down-regulate SLAMF6$^{var1}$ expression. In another embodiment the cell population has been engineered to express SLAMF6$^{var3}$ exogenously.

In another aspect, there is provided a method of generating a therapeutic cell composition, comprising:
a) obtaining a cell population selected from the group consisting of: T cells, tumor cells and DC; and
b) modulating the cells ex vivo to express preferentially SLAMF6$^{var3}$.

In another aspect there is provided an isolated human SLAMF6$^{var3}$ ectodomain for use in treating cancer in a human subject in need thereof. In one embodiment the use comprises administration to said subject in an amount effective to treat cancer in said subject. In another embodiment the use comprises contacting T cells of said subject ex vivo with said isolated human SLAMF6$^{var3}$ ectodomain in an amount effective to expand and/or activate said T cells, and adoptively transferring the resulting T cells to said subject to thereby treat cancer in said subject.

In another aspect, the invention provides a method for treating cancer in a human subject in need thereof, comprising administering to the subject, or contacting with T cells of said subject, an effective amount of an isolated human SLAMF6$^{var3}$ ectodomain, thereby treating cancer in said subject. In one embodiment, the method comprises administering to said subject an effective amount of an isolated human SLAMF6$^{var3}$ ectodomain. In another embodiment, the method comprises contacting T cells of said subject ex vivo with the isolated SLAMF6$^{var3}$ ectodomain in an amount effective to expand and/or activate said T cells, and adoptively transferring the resulting T cells to said subject to thereby treat cancer in said subject.

In another aspect there is provided a chimeric polypeptide precursor comprising an isolated human SLAMF6$^{var3}$ ectodomain fused to an N' SLAMF6$^{var1}$ signal peptide. In one embodiment the polypeptide precursor has the amino acid sequence as set forth in SEQ ID NO: 15. In another embodiment said polypeptide precursor is encoded by a polynucleotide as set forth in SEQ ID NO: 19. In another embodiment, there is provided a polynucleotide encoding the polypeptide precursor disclosed herein. In a particular embodiment the polynucleotide sequence is as set forth in SEQ ID NO: 19. In another embodiment there is provided an isolated human SLAMF6$^{var3}$ ectodomain produced by a process comprising expressing the polypeptide precursor in a mammalian expression system and isolating the resulting ectodomain polypeptide. In another embodiment the invention relates to the polypeptide precursor as disclosed herein for use in treating cancer in a human subject in need thereof.

Other objects, features and advantages of the present invention will become clear from the following description and drawings.

BRIEF DESCRIPTION OF THE DRAWINGS

FIG. 2A—results of two independent experiments. FIG. 2B—summary of the combined data from the three TILs in the two experiments. Two-tailed t test * p<0.05; ***p<0.0001

FIG. 3A dot plots, FIG. 3B - summary of triplicates showing percentage positive cells. Two-tailed t test * p<0.05; ** p<0.01

FIG. 4A—mRNA was extracted from human PBMCs, Jurkat cells and CD8$^+$ TILs. Jurkat cells were activated with PMA and ionomycin. RT-PCR was performed with primers designed to produce PCR products with differing sizes for different SLAMF6 variants (var1–SLAMF6$^{var1}$+ SLAMF6$^{var2}$; var3 –SLAMF6$^{var3}$, var4–SLAMF6$^{var4}$). FIG. 4B-for quantitative RT-PCR, RNA was isolated from Jurkat cells (non-activated or activated by PMA and ionomycin), transcribed to cDNA using qScript cDNA Synthesis kit, and real time PCR was performed using PerfeCT SYBR Green FastMIX ROX.

FIG. 9A—Pmel mouse splenocytes were expanded in vitro with their cognate antigen and IL2 and maintained for 4 additional days with medium supplemented with IL-2, seSLAMF6-V3 or with culture medium alone (no treatment; "No t"). % viable cells (Annexin V$^-$/PI$^-$) were determined by flow cytometry. FIG. 9B—Averaged values of triplicates showing % viable cells. Two-tailed t test **p<0.01.

DETAILED DESCRIPTION OF THE INVENTION

Figure 1:
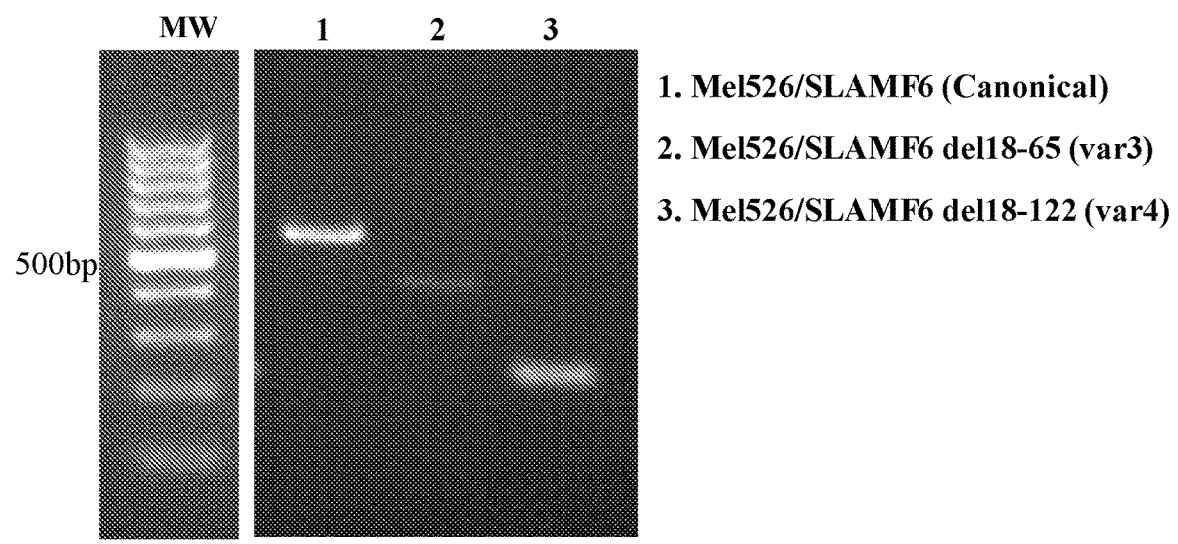
FIG. 1. Aberrant expression of SLAMF6 splice variants in melanoma cell lines. mRNA was extracted from SLAMF6-transfected melanoma cell lines. RT-PCR was performed with primers designed to span canonical, var3 and var4 mRNA splice variants.

The invention relates to cancer immunotherapy, particularly to improved therapeutic modalities involving the modulation of expression and/or activity of SLAMF6 splice variants. More specifically, embodiments of the invention provide compositions and methods for cancer therapy of human subjects, including adoptive T cell transfer therapies, tumor cell vaccines and/or polypeptide-based medicaments.

The invention is based, in part, on the surprising discovery that differential modulation of the expression and/or activity of specific human SLAMF6 variants provides for improved cancer therapy. In particular, various SLAMF6 isoforms were found to be concomitantly expressed in resting and activated T cells, and to manifest distinct and even opposing biological effects in the context of anti-tumor immunity. Specifically, it is now disclosed for the first time that a splice variant of human SLAMF6, which lacks a part of exon 2 that encodes a sequence of the extracellular domain, namely SLAMF6 variant 3 (SLAMF6$^{var3}$), exerts a strong agonistic effect on T cell activity and anti-tumor immunity. In contradistinction, other SLAMF6 variants, including canonical human SLAMF6 (variant 1, SLAMF6$^{var1}$), and a splice variant lacking a larger portion of exon 2 (variant 4, SLAMF6$^{var4}$), either exerted significantly weaker agonistic effects, or even mediated down-regulating effects, resulting in reduced anti-tumor immunity, as detailed hereinbelow.

More specifically, it was unexpectedly found that engineering human melanoma cells to aberrantly express SLAMF6$^{var3}$ leads to enhanced anti-melanoma human CD8$^+$ T-cell activity, compared to their activity towards non-transfected cells. In contradistinction, aberrant expression of other SLAMF6 variants did not result in such enhancement, or even resulted in reduced anti-melanoma activity. In addition, it was surprisingly found that specific down-regulation of SLAMF6$^{var1}$ expression by gene editing, while normal SLAMF6$^{var3}$ expression level is retained, leads to marked enhancement of T cell responses to activation stimuli. Non-specific down-regulation of multiple SLAMF6 variants, including those characterized by deletions at exon 2 and those lacking such deletions, did not result in such enhancement.

The invention is further based, in part, on experiments performed using an isolated polypeptide comprising a human SLAMF6$^{var3}$ ectodomain (seSLAMF6$^{var3}$). In particular, seSLAMF6$^{var3}$ was effective in providing T cell co-stimulation as well as in reducing activation-induced T cell death, in both murine and human T cells. In addition, it was surprisingly found that seSLAMF6$^{var3}$ bound to an isolated SLAMF$^{var1}$ ectodomain with a greater affinity than the homotypic binding identified for the SLAMF6$^{var1}$ ectodomain.

Thus, SLAMF6 was originally described as a dual receptor, with an activating or inhibitory effect attributed to its intracellular tyrosine switch motifs (ITSM). The present disclosure, however, unexpectedly demonstrates that the extracellular part of the receptor determines the direction of the immune response in human T cells. In particular, the invention demonstrates that while T cell-mediated treatment of tumors expressing SLAMF6 may be less effective than the treatment of tumors lacking substantial SLAMF6 surface expression, specific augmentation of SLAMF6$^{var3}$ expression or activity on T cells and/or tumor cells provides for improved treatment efficacy.

Accordingly, embodiments of the invention are directed to methods for the treatment of cancer in a subject in need thereof. According to these embodiments, the methods of the invention are effected by providing a SLAMF6$^{var3}$-directed T cell stimulation to the subject, e.g. by administering to said subject an isolated SLAMF6$^{var3}$ ectodomain, a T-cell composition manipulated ex vivo to augment SLAMF6$^{var3}$-directed T cell stimulation, and/or a cell vaccine engineered to express selectively or preferentially SLAMF6$^{var3}$, as will be described in further detail below. Without wishing to be bound by a specific theory or mechanism of action, engagement (binding) of human T cells by a cell-surface expressed SLAMF6$^{var3}$ molecule (in trans), or by an isolated (soluble, cell-free) SLAMF6$^{var3}$ ectodomain, modulates intracellular signaling, to thereby stimulate said T cells. According to various embodiments, the methods comprise selective or preferential engagement of SLAMF6$^{var3}$ on T cells of said subject so as to provide the SLAMF6$^{var3}$-directed T cell stimulation. According to a preferred embodiment, said methods comprise providing a SLAMF6$^{var3}$-directed T cell stimulation without substantially providing a SLAMF6$^{var1}$-directed T cell stimulation. In other embodiments, the methods comprise administration of SLAMF6$^{var3}$ or an ectodomain thereof (e.g. by incubating or otherwise contacting a T cell population with cell surface-expressed SLAMF6$^{var3}$ or with an isolated SLAMF6$^{var3}$ ectodomain) to thereby stimulate the T cells. According to various embodiments, the SLAMF6$^{var3}$-directed T cell stimulation is provided by administering to said subject an isolated SLAMF6$^{var3}$ ectodomain, a T-cell composition manipulated ex vivo to augment SLAMF6$^{var3}$-directed T cell stimulation, and/or a cell vaccine engineered to express selectively or preferentially SLAMF6$^{var3}$, as described in further detail herein.

In some embodiments, said stimulation comprises administering to said subject (or contacting T cells of the subject with) an isolated SLAMF6$^{var3}$ ectodomain (or a specific agonist thereof), thereby treating cancer in said subject. Thus, in one aspect, there is provided a method for treating cancer in a subject in need thereof, comprising administering to the subject an isolated SLAMF6$^{var3}$ ectodomain, thereby treating cancer in said subject. In a particular embodiment, said method comprises administering to said subject an isolated human SLAMF6$^{var3}$ ectodomain.

In another aspect there is provided an isolated human SLAMF6$^{var3}$ ectodomain for use in treating cancer in a human subject in need thereof. In one embodiment the use comprises administration to said subject in an amount effective to treat cancer in said subject. In another embodiment the use comprises contacting T cells of said subject ex vivo with said isolated human SLAMF6$^{var3}$ ectodomain in an amount effective to expand and/or activate said T cells, and adoptively transferring the resulting T cells to said subject to thereby treat cancer in said subject.

According to other embodiments, the therapeutic methods of the invention provide for cancer treatment by adoptive T cell transfer therapy. In various embodiments, the treatment is provided by administering (adoptively transferring) to said subject a T-cell composition manipulated ex vivo to augment SLAMF6$^{var3}$-directed T cell stimulation, thereby treating cancer in said subject. In various embodiments, the manipulation comprises specifically enhancing SLAMF6$^{var3}$ expression, specifically enhancing SLAMF6$^{var3}$ activity, specifically reducing SLAMF6$^{var1}$ expression, or any combination thereof.

Thus, in another aspect, there is provided a method for treating cancer in a subject in need thereof, comprising administering to the subject T cells engineered to express preferentially (also referred to herein as "differentially") SLAMF6$^{var3}$.

In another embodiment of the adoptive transfer methods of the invention, said T cells are autologous. In another embodiment, said T cells are allogeneic, typically histocompatible with the subject to be treated. In other embodiments, said T cells are selected from the group consisting of tumor-infiltrating lymphocytes (TIL), peripheral blood mononuclear cells (PBMC), and an engineered T cell line (e.g. expressing a chimeric antigen receptor). In another embodiment said T cells comprise CD8$^+$ T cells. In another embodiment said T cells comprise CD8$^+$ T cells and CD4$^+$ T cells. In yet other embodiments, said T cells are purified CD8$^+$ T cells or CD4$^+$ T cells.

In another embodiment, the method comprises:
a) obtaining T cells form the subject, or from a donor histocompatible with the subject;
b) modulating the cells ex vivo to express preferentially SLAMF6$^{var3}$;
c) adoptively transferring the resulting T cells to said subject to thereby treat cancer in said subject.

Non-limitative means for generating and selecting T cell populations modulated to express preferentially SLAMF6$^{var3}$ that are suitable for use in the methods of the invention are available, e.g. as disclosed and exemplified herein. For example, without limitation, Example 2 herein demonstrates generation and selection of a T cell population in which the mRNA ratio of SLAMF6$^{var3}$ to SLAMF6$^{var1}$ has been increased to be approximately 1:1, wherein said T cell population exhibits an average 4.5-fold increase in IL-2 secretion in response to activation (by PMA and ionomycin, compared to non-manipulated T cells).

According to yet other embodiments, the therapeutic methods of the invention provide for cancer treatment using tumor cell vaccination. Thus, in other embodiments, said activation comprises administering to said subject a tumor cell vaccine engineered (or otherwise manipulated) to express preferentially SLAMF6$^{var3}$. For example, tumor cells lacking substantial expression of SLAMF6 and/or variants thereof (e.g. solid tumors) may be engineered to express exogenous SLAMF6$^{var3}$, whereas tumor cells expressing SLAMF6 and/or variants thereof (e.g. hematopoietic tumors) may be manipulated as described above with respect to T cells to selectively up-regulate SLAMF6$^{var3}$ expression and/or selectively down-regulate SLAMF6$^{var1}$ expression. Such tumor cell vaccines are prepared by suitable protocols, including irradiation or otherwise attenuation prior to administration to said subject. In another embodiment, the use of dendritic cell (DC) vaccines expressing preferentially SLAMF6$^{var3}$ is contemplated. Such DC vaccines are loaded with suitable tumor antigens prior to administration to the subject, and are typically histocompatible with said subject. Cell vaccines are administered by suitable immunization protocols, optionally in conjunction with adjuvants or other immune modulators. In a particular embodiment, the tumor cell vaccine is a melanoma cell vaccine.

Other embodiments of the invention are directed to improved cell compositions for cancer therapy. According to various embodiments, the invention provides for cell compositions useful for adoptive transfer and/or vaccination. In various embodiments, the invention provides T cell compositions and cell vaccines engineered (or otherwise manipulated) to express preferentially SLAMF6$^{var3}$, as detailed herein. In other embodiments, the invention relates to methods for generating said improved cell compositions and vaccines, as detailed herein. In other embodiments, there is provided a pharmaceutical composition for cancer immunotherapy, comprising a therapeutically effective amount of a SLAMF6$^{var3}$ ectodomain, and a pharmaceutically acceptable carrier or excipient.

Thus, in another aspect, the invention provides a therapeutic cell composition comprising a cell population engineered to express preferentially SLAMF6$^{var3}$. In various embodiments, the composition is selected from the group consisting of: an adoptive transfer T cell composition, a tumor cell vaccine and a DC vaccine. In one embodiment the cell population is a human T cell population and the composition is an adoptive transfer T cell composition. In another embodiment the cell population is a human tumor cell population and the cell vaccine is a tumor cell vaccine. In a particular embodiment said tumor cell population is a melanoma cell population. In yet another embodiment the cell population is a human DC population and the cell vaccine is a DC vaccine. In another embodiment the cell population has been engineered to selectively up-regulate SLAMF6$^{var3}$ expression. In another embodiment, the cell population has been engineered to selectively down-regulate SLAMF6$^{var1}$ expression. In yet another embodiment, the cell population has been engineered to selectively up-regulate SLAMF6$^{var3}$ expression and to selectively down-regulate SLAMF6$^{var1}$ expression. In another embodiment the cell population has been engineered to express SLAMF6$^{var3}$ exogenously.

In another aspect, there is provided a therapeutic cell composition comprising a cell population engineered to express preferentially SLAMF6$^{var3}$ as described herein, for use in treating cancer in a human subject in need thereof In one embodiment the cell population is a human T cell population and said composition is an adoptive transfer T cell composition, and wherein said T cells are autologous, or are allogeneic T cells histocompatible with said subject. In another embodiment said T cells have been generated by a method comprising modulating ex vivo T cells of the subject, or of a donor histocompatible with said subject, to express preferentially SLAMF6$^{var3}$, and formulating the resulting T cells as an adoptive transfer composition for cancer treatment. In another embodiment said T cells have been further expanded and/or activated by incubation with an isolated SLAMF6$^{var3}$ ectodomain. In another embodiment the cell population is a human tumor cell population and the cell vaccine is a tumor cell vaccine. In another embodiment the tumor cell population is a melanoma cell population. In another embodiment the cell population is a DC population and the cell vaccine is a DC vaccine.

In another aspect, there is provided a method of generating a therapeutic cell composition, comprising:
   a) obtaining a cell population selected from the group consisting of: T cells, tumor cells and DC; and
   b) modulating the cells ex vivo to express preferentially SLAMF6$^{var3}$.

In another aspect there is provided a chimeric polypeptide precursor comprising an isolated human SLAMF6$^{var3}$ ectodomain fused to an N' SLAMF6$^{var1}$ signal peptide. In one embodiment the polypeptide precursor has the amino acid sequence as set forth in SEQ ID NO: 15. In another embodiment said polypeptide precursor is encoded by a polynucleotide as set forth in SEQ ID NO: 19. In another embodiment, there is provided a polynucleotide encoding the polypeptide precursor. In a particular embodiment the polynucleotide sequence is as set forth in SEQ ID NO: 19. In another embodiment there is provided an isolated human SLAMF6$^{var3}$ ectodomain produced by a process comprising expressing the polypeptide precursor in a mammalian expression system and isolating the resulting ectodomain polypeptide. In another embodiment the invention relates to the polypeptide precursor as disclosed herein for use in treating cancer in a human subject in need thereof.

SLAMF6 Variants

Generally, SLAMF6 is comprised of the following domains in the order of N' to C':
   I. an N-terminal signal peptide;
   II. an extracellular portion (ectodomain), comprising two conserved immunoglobulin (Ig)-like motifs: an N' Ig-like V-type domain (IgV, having a two-layered β-sheet structure, with predominantly neutral, albeit polar, front surfaces), and a C' Ig-like C2-type domain (IgC2, characterized by an overall β-strand topology and several disulfide bonds);
   III. a helical transmembrane domain; and
   IV. a topological (cytoplasmic) domain, containing immunoreceptor tyrosine-based switch motifs (ITSMs), which are docking sites for the SH2 domain of SLAM-associated protein (SAP) and the related Ewing's sarcoma-associated transcript. ITSM motifs carry the consensus sequence TxYxxV/I/L that have overlapping specificity for activating and inhibitory binding partners.

In canonical human SLAMF6 (e.g. accession no. Q96DU3, isoform 1), the signal peptide has been identified to be located at positions 1-21 of the transcribed polypeptide, the ectodomain has been identified to be located at positions 22-226 (wherein IgV was located at positions 35-120 and IgC2 at positions 132-209), the transmembrane domain was located at positions 227-247, and the cytoplasmic (intracellular) domain—at positions 248-331. Exon 2 encodes for the amino acids at positions 17-127.

The amino acid sequence of human SLAMF6$^{var1}$ (precursor, also provided in accession no. NM_001184714.1), is as follows:

(SEQ ID NO: 1)
MLWLFQSLLFVFCFGPGNVVSQSSLTPLMVNGILGESVTLPLEFPAGEKV

NFITWLFNETSLAFIVPHETKSPEIHVTNPKQGKRLNFTQSYSLQLSNLK

MEDTGSYRAQISTKTSAKLSSYTLRILRQLRNIQVTNHSQLFQNMTCELH

LTCSVEDADDNVSFRWEALGNTLSSQPNLTVSWDPRISSEQDYTCIAENA

VSNLSFSVSAQKLCEDVKIQYTDTKMILFMVSGICIVFGFIILLLLVLRK

RRDSLSLSTQRTQGPAESARNLEYVSVSPTNNTVYASVTHSNRETEIWTP

RENDTITIYSTINHSKESKPTFSRATALDNVV.

Human SLAMF6$^{var2}$ differs from SLAMF6$^{var1}$ by deletion of a single alanine at position 266 relative to SEQ ID NO: 1.

Human SLAMF6$^{var3}$ (precursor, NM_001184715.1) differs from SLAMF6$^{var1}$ be deletion of amino acids (aa) 17-65 relative to SEQ ID NO: 1. The deletion includes aa 17-21 residing in the signal peptide (i.e. the penta-peptide GNVVS (SEQ ID NO: 20)), and aa 22-65, residing in the ectodomain. The precursor sequence denoted by accession number NM_001184715.1 is as follows:

(SEQ ID NO: 16)
MLWLFQSLLFVFCFGPVPHETKSPEIHVTNPKQGKRLNFTQSYSLQLSNL

KMEDTGSYRAQISTKTSAKLSSYTLRILRQLRNIQVTNHSQLFQNMTCEL

HLTCSVEDADDNVSFRWEALGNTLSSQPNLTVSWDPRISSEQDYTCIAEN

AVSNLSFSVSAQKLCEDVKIQYTDTKMILFMVSGICIVFGFIILLLLVLR

KRRDSLSLSTQRTQGPESARNLEYVSVSPTNNTVYASVTHSNRETEIWTP

RENDTITIYSTINHSKESKPTFSRATALDNV,

Human SLAMF6$^{var4}$ (precursor, NM_001184716.1, SEQ ID NO: 17) differs from SLAMF6$^{var1}$ by deletion of aa 17-128 relative to SEQ ID NO: 1.

Therefore, the amino acid sequence of an isolated ectodomain of human SLAMF6$^{var3}$, useful in embodiments of the invention, is as follows:

(SEQ ID NO: 18)
KSPEIHVTNPKQGKRLNFTQSYSLQLSNLKMEDTGSYRAQISTKTSAKLS

SYTLRILRQLRNIQVTNHSQLFQNMTCELHLTCSVEDADDNVSFRWEALG

NTLSSQPNLTVSWDPRISSEQDYTCIAENAVSNLSFSVSAQKLCEDVKIQ

YTDTKM.

The amino acid sequence of an isolated ectodomain of human SLAMF6$^{var3}$, useful in additional embodiments of the invention, is as follows:

(SEQ ID NO: 14)
VPHETKSPEIHVTNPKQGKRLNFTQSYSLQLSNLKMEDTGSYRAQISTKT

SAKLSSYTLRILRQLRNIQVTNHSQLFQNMTCELHLTCSVEDADDNVSFR

WEALGNTLSSQPNLTVSWDPRISSEQDYTCIAENAVSNLSFSVSAQKLCE

DVKIQYTDTKM.

The terms "ectodomain" as used herein refers to the extracellular, surface exposed portion of a SLAMF6 polypeptide, comprising at least the IgV and the IgC2 domains. Typically and advantageously, a SLAMF6$^{var3}$ ectodomain used in the methods and compositions of the invention substantially excludes other SLAMF6 domains as described herein, such as the signal peptide, the transmembrane domain and the topological domain. Such an advantageous polypeptide is referred to herein as an "isolated SLAMF6$^{var3}$ ectodomain". An isolated SLAMF6$^{var3}$ ectodomain is typically and conveniently produced synthetically, e.g. by recombinant methods as described herein. In other words, while isolated SLAMF6$^{var3}$ ectodomain polypeptides may contain residual SLAMF6 sequences (e.g. 1-10 and preferably 5 or less amino acids), they lack any additional SLAMF6 structures that function as they would in the intact SLAMF6 polypeptide (such as the complete functional domains described herein). In other examples of isolated SLAMF6$^{var3}$ ectodomain polypeptides, such residual SLAMF6 sequences (e.g. up to about 10 aa) are arranged within the polypeptide in a non-contiguous manner, i.e. in an order or configuration which differs from that of naturally occurring SLAMF6$^{var3}$. A non-limitative example of such engineered polypeptides is represented by the chimeric polypeptide constructs described in further detail below. In addition, a particularly advantageous SLAMF6$^{var3}$ ectodomain as referred to in embodiments of the invention lacks aa 17-65 or 18-65, but retains aa 66-128, relative to SEQ ID NO: 1.

In certain embodiments, the SLAMF6$^{var3}$ ectodomain may be conjugated to or fused with additional exogenous sequences, including but not limited to an epitope tag (e.g. poly-histidine tag) and/or a plasma half-life elongating moiety. An exemplary sequence of an isolated SLAMF6$^{var3}$ ectodomain suitable for recombinant production in a mammalian expression system is set forth in SEQ ID NO: 15 herein. The encoded sequence comprises an N' signal peptide, a human SLAMF6$^{var3}$ ectodomain, and a C' 6-histidine tag, useful for isolation of the expressed polypeptide, as described in Example 3 herein.

Specifically, as described herein, the polypeptide as set forth in SEQ ID NO: 15 (and encoded by a polynucleotide as set forth in SEQ ID NO: 19), is a chimeric polypeptide precursor comprising an isolated human SLAMF6$^{var3}$ ectodomain fused to an N' SLAMF6$^{var1}$ signal peptide. As further disclosed and exemplified in certain embodiments herein, when expressed in a mammalian expression system (HEK293 cells), a construct encoding a polypeptide of SEQ ID NO: 15 yielded an isolated human SLAMF6$^{var3}$ ectodomain retaining part of the heterologous signal peptide.

Polypeptides and peptides useful in embodiments of the invention (e.g. SLAMF6$^{var3}$ ectodomain) may be isolated or synthesized using any recombinant or synthetic method known in the art. For instance, peptides or polypeptide fragments may be synthesized by methods including, but not limited to, solid phase (e.g. Boc or f-Moc chemistry) and solution phase synthesis methods. For example, peptides can be synthesized by a solid phase peptide synthesis method of Merrifield (1963, J Am Chem Soc 85, 2149). Alternatively, a peptide can be synthesized using standard solution methods well known in the art or by any other method known in the art for peptide synthesis.

Polypeptides and peptides may conveniently be produced by recombinant technology. Recombinant methods for designing, expressing and purifying proteins and peptides are known in the art (see, e.g. Sambrook et al., 2001, Molecular Cloning: A Laboratory Manual, Cold Springs Harbor Laboratory, New York). Nucleic acid molecules may include DNA, RNA, or derivatives of either DNA or RNA. An isolated nucleic acid sequence encoding a polypeptide or peptide can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, modified nucleic acid sequences in which nucleotides have been inserted, deleted, substituted, and/or inverted in such a manner that such modifications do not substantially interfere with the nucleic acid molecule's ability to encode a functional product. A polynucleotide or oligonucleotide sequence can be deduced from the genetic code of a protein, however, the degeneracy of the code must be taken into account, as well as the allowance of exceptions to classical base pairing in the third position of the codon, as given by the so-called "Wobble rules". Polynucleotides that include more or less nucleotides can result in the same or equivalent proteins. Using recombinant production methods, selected host cells, e.g. of a microorganism such as E. coli or yeast, are transformed with a hybrid viral or plasmid DNA vector including a specific DNA sequence coding for the polypeptide and the polypeptide is synthesized in the host upon transcription and translation of the DNA sequence.

In another aspect, the methods of the invention may be affected by expressing in a cell population obtained from a subject SLAMF6$^{var3}$ or an isolated polypeptide comprising a SLAMF6$^{var3}$ ectodomain (e.g. by isolating cells from a subject, introducing a vector capable of expressing the polypeptide of interest and re-introducing the cells into the subject). With respect to expression of SLAMF6$^{var3}$ ectodomain, the vector is designed such that the polypeptide is secreted in the subject and is capable of contacting the subject's T cells).

The preparation of expression constructs or vectors used for delivering and expressing a desired gene product are known in the art. Such construct typically comprise regulatory sequences or selectable markers, as known in the art. The nucleic acid construct (also referred to herein as an "expression vector") may include additional sequences that render this vector suitable for replication and integration in prokaryotes, eukaryotes, or optionally both (e.g., shuttle vectors). In addition, a typical cloning vector may also contain transcription and translation initiation sequences, transcription and translation terminators, and a polyadenylation signal.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, and pNMT81, which are available from Invitrogen, pCI which is available from Promega, pMbac, pPbac, pBK-RSV and pBK-CMV, which are available from Stratagene, pTRES which is available from Clontech, and their derivatives. These may serve as vector backbone for the constructs useful in embodiments described herein.

Recombinant viral vectors are useful for in vivo expression of the genes of the present invention since they offer advantages such as lateral infection and targeting specificity. Lateral infection is inherent in the life cycle of retrovirus, for example, and is the process by which a single infected cell produces many progeny virions that bud off and infect neighboring cells. The result is the rapid infection of a large area of cells, most of which were not initially infected by the original viral particles. This is in contrast to vertical-type infection in which the infectious agent spreads only through daughter progeny. Viral vectors can also be produced that are unable to spread laterally. This characteristic can be useful if the desired purpose is to introduce a specified gene into only a localized number of targeted cells.

In certain exemplary embodiments, an isolated human SLAMF6$^{var3}$ ectodomain produced by a process comprising expressing a chimeric polypeptide precursor as described herein in a mammalian expression system and isolating the resulting ectodomain polypeptide, may retain up to 11 N' aa residues of its heterologous signal peptide sequence as described herein (e.g. 1-11, 1-10, 5-11 or in other embodiments 5, 6, 7 or 8 residues). In some embodiments, said isolated human SLAMF6$^{var3}$ ectodomain retains at least the penta-peptide GNVVS (SEQ ID NO: 20).

Cell Engineering

According to certain embodiments, the invention relates to cell engineering, and to compositions and methods in which a chosen cell population is modified or manipulated to differentially alter the expression of SLAMF6 isoforms. In particular, embodiments of the invention utilize cells engineered to express preferentially SLAMF6$^{var3}$. In certain particular embodiments, the cell population is selected from the group consisting of: T cells, tumor cells and dendritic cells (DC). Such cells are produced in some embodiments using genetic engineering or other forms of ex-vivo modulation, as detailed herein.

In certain embodiments, the cells have been engineered to selectively down-regulate SLAMF6$^{var1}$ expression. Thus, embodiments of the invention employ the use of genome editing, genome silencing or post-transcriptional regulation of gene expression, e.g. by engineering tools including but not limited to a plasmid, an artificially engineered restriction enzyme, a plasmid specifically encoding a meganuclease, or a tool for transcriptional or post-transcriptional gene regulation. In certain embodiments, the use of a tool selected from the group consisting of an antisense molecule, a RNA interference (RNAi) molecule (e.g. small interfering RNAs (siRNAs) and hairpin RNAs) and an enzymatic nucleic acid molecule (e.g. ribozymes and DNAzymes), is contemplated. In other specific embodiments, the use of gene editing agents (e.g. Cas9/gRNA RNP) is contemplated. Non-limitative examples for the use of such agents for selectively down-regulating SLAMF6$^{var1}$ expression are provided in the Examples section below.

RNA interference is a two-step process. During the first step, which is termed the initiation step, input dsRNA is digested into 21-23 nucleotide (nt) small interfering RNAs (siRNA), probably by the action of Dicer, a member of the RNase III family of dsRNA-specific ribonucleases, which cleaves dsRNA (introduced directly or via an expressing vector, cassette or virus) in an ATP-dependent manner.

Successive cleavage events degrade the RNA to 19-21 bp duplexes (siRNA), each strand with 2-nucleotide 3' overhangs.

In the effector step, the siRNA duplexes bind to a nuclease complex to form the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA. Although the mechanism of cleavage is still to be elucidated, research indicates that each RISC contains a single siRNA and an RNase.

It is possible to eliminate the "initiation step" by providing a priori siRNA. Because of the remarkable potency of RNAi, an amplification step within the RNAi pathway has been suggested. Amplification could occur by copying of the input dsRNAs, which would generate more siRNAs, or by replication of the siRNAs formed. Alternatively or additionally, amplification could be effected by multiple turnover events of the RISC.

Synthesis of RNAi molecules suitable for use with the present invention can be effected as follows. First, the nucleic acid sequence target is optionally scanned downstream for AA dinucleotide sequences. Occurrence of each AA and the 3' adjacent 19 nucleotides is recorded as potential siRNA target sites. Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites that exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

Antisense oligonucleotides are nucleic acids that are complementary (or antisense) to the coding strand (sense strand) of the mRNA encoding a particular protein (also known as the negative strand). Although antisense oligonucleic acids are typically RNA based, they can also be DNA based. Additionally, antisense oligonucleotides are often modified to increase their stability. These modifications are known in the art and include, but are not limited to modifying the backbone of the oligonucleotide, modifying the sugar moieties, or modifying the base. Also inclusive in these modifications are various DNA-RNA hybrids or constructs commonly referred to as "gapped" oligonucleotides.

Without being bound by theory, the binding of these antisense molecules to the mRNA is believed to induce stretches of double stranded RNA that trigger degradation of the messages by endogenous RNAses. Alternatively, ribosomes, which are in the process of making the protein from the RNA, are blocked from progressing as they cannot move along the regions of double stranded RNA that are formed. Additionally, sometimes the oligonucleotides are specifically designed to bind near the promoter of the message, and under these circumstances, the antisense oligonucleotides may additionally interfere with translation of the message.

Regardless of the specific mechanism by which antisense oligonucleotides function, their administration to a cell or tissue allows the degradation of the mRNA encoding a specific protein or prevention of its translation. Accordingly, antisense molecules decrease the expression and/or activity of a particular protein.

To design an antisense oligonucleic acid that specifically binds to and mediates the degradation of a particular protein, it is important that the sequence recognized by the oligonucleic acid is unique or substantially unique to that particular protein. For example, sequences that are frequently repeated across protein may not be an ideal choice for the design of an oligonucleic acid that specifically recognizes and degrades a particular message. One skilled in the art can design an oligonucleic acid, and compare the sequence of that oligonucleic acid to nucleic acid sequences that are deposited in publicly available databases to confirm that the sequence is specific or substantially specific for a particular protein.

Methods of producing antisense oligonucleotides may be found for example, in U.S. Pat. Nos. 7,022,832; 6,972,171; 6,277,981 and US Patent Application Publication No. 20050261485.

In some embodiments, the antisense oligonucleotide may be designed to induce exon skipping (e.g. of exon 2) by methods known in the art, thereby down-regulating SLAMF6$^{var1}$ expression.

The terms "enzymatic nucleic acid molecule" or "enzymatic oligonucleic acid" refers to a nucleic acid molecule which has complementarity in a substrate binding region to a specified gene target, and also has an enzymatic activity which is active to specifically cleave target RNA, thereby silencing the target gene. The complementary regions allow sufficient hybridization of the enzymatic nucleic acid molecule to the target RNA and subsequent cleavage. The term enzymatic nucleic acid is used interchangeably with for example, ribozymes, catalytic RNA, enzymatic RNA, catalytic DNA, aptazyme or aptamer-binding ribozyme, catalytic oligonucleotide, nucleozyme, DNAzyme, RNAenzyme.

The possibility of designing ribozymes to cleave any specific target RNA has rendered them valuable tools in both basic research and therapeutic applications. In therapeutics, ribozymes have been exploited to target viral RNAs in infectious diseases, dominant oncogenes in cancers, and specific somatic mutations in genetic disorders Ribozymes and ribozyme analogs are described, for example, in U.S. Pat. Nos. 5,436,330; 5,545,729 and 5,631,115.

Genome editing is a method in which endogenous chromosomal sequences present in one or more cells (including within a subject), can be edited, e.g., modified, using targeted endonucleases and single-stranded nucleic acids. The genome editing method can result in the insertion of a nucleic acid sequence at a specific region within the genome, the excision of a specific sequence from the genome and/or the replacement of a specific genomic sequence with a new nucleic acid sequence. For example, and not by way of limitation, the genome editing method can include the use of a guide RNA (gRNA), including protospacer adjacent motifs (PAMs), complementary to a specific sequence within a genome, e.g., a chromosomal breakpoint associated with a fusion gene, to guide a nuclease, e.g., an endonuclease, to the specific genomic sequence. A non-limiting example of an endonuclease includes CRISPR associated protein 9 (Cas9). The endonuclease can result in the cleavage of the targeted genome sequence and allow modification of the genome at the cleavage site through nonhomologous end joining (NHEJ) or homologous recombination. A non-limiting example of genome editing method is disclosed in PCT Application No. WO 2014/093701, the contents of which is hereby incorporated by reference in its entirety.

One non-limiting example of a CRISPR/Cas system used to inhibit gene expression, CRISPRi, is described in U.S. Patent Appl. Publ. No. US20140068797. CRISPRi induces permanent gene disruption that utilizes the RNA-guided Cas9 endonuclease to introduce DNA double stranded breaks, which trigger error-prone repair pathways to result in frame shift mutations. A catalytically dead Cas9 lacks endonuclease activity. When coexpressed with a guide RNA, a DNA recognition complex is generated that specifically interferes with transcriptional elongation, RNA polymerase binding, or transcription factor binding. This CRISPRi system efficiently represses expression of targeted genes. CRISPR/Cas gene disruption occurs when a guide nucleotide sequence specific for a target gene and a Cas endonuclease are introduced into a cell and form a complex that enables the Cas endonuclease to introduce a double strand break at the target gene. In certain embodiments, the CRISPR/Cas system comprises an expression vector. In other embodiments, the Cas expression vector induces expression of Cas9 endonuclease. Other endonucleases may also be used, including but not limited to, T7, Cas3, Cas8a, Cas8b, CaslOd, Csel, Csyl, Csn2, Cas4, CaslO, Csm2, Cmr5, Fokl, other nucleases known in the art, and any combinations thereof.

Additionally or alternatively, the cells have been engineered to selectively up-regulate SLAMF6$^{var3}$ expression. In a particular embodiment, the cells have been engineered to express SLAMF6$^{var3}$ (e.g. human SLAMF6$^{var3}$) exogenously. Thus, embodiments of the invention employ the use of expression constructs and vectors as described herein, including but not limited to plasmids and viral vectors, to induce or enhance SLAMF6$^{var3}$ expression.

It is to be understood, that in cells engineered to selectively down-regulate SLAMF6$^{var1}$ expression, no substantial down-regulation of SLAMF6$^{var3}$ has been exerted. Similarly, in cells engineered to selectively up-regulate SLAMF6$^{var3}$ expression, no substantial up-regulation of SLAMF6$^{var1}$ is exerted. Accordingly, a cell engineered to express preferentially SLAMF6$^{var3}$ is typically characterized by an augmented ratio of SLAMF6$^{var3}$ to SLAMF6$^{var1}$ expression. Thus, in some embodiments, selective down-regulation of SLAMF6$^{var1}$ expression may be accompanied by down-regulation of SLAMF6$^{var2}$.

In yet other embodiments the invention additionally or alternatively includes engineering the T cells, tumor cells and/or DC used in compositions and methods of the invention to selectively up-regulate SLAMF6$^{var4}$ expression. In yet further embodiments, the invention additionally or alternatively employs administration of an isolated SLAMF6$^{var4}$ ectodomain.

In another aspect there is provided a method for treating cancer in a human subject in need thereof, comprising administering to the subject T cells engineered to selectively down-regulate SLAMF6$^{var1}$ expression.

In another embodiment, the method comprises:
a) obtaining T cells form the subject, or from a donor histocompatible with the subject;
b) modulating the cells ex vivo to selectively down-regulate SLAMF6$^{var1}$ expression; and
c) adoptively transferring the resulting T cells to said subject to thereby treat cancer in said subject.

In another aspect the invention provides a therapeutic cell composition comprising a cell population engineered to selectively down-regulate SLAMF6$^{var1}$ expression.

In other embodiments, the modulation may be effected in vivo. Thus, in some embodiments there is provided a method for treating cancer in a human subject in need thereof, comprising in vivo manipulating cells of the subject (e.g. T cells, tumor cells or DC) to express preferentially SLAMF6$^{var3}$. In various embodiments, the manipulation is performed by methods known in the art, including but not limited to gene therapy, genome editing, exon skipping and the like. For example, without limitation, the methods may be performed by administering to the subject an expression vector inducing or enhancing the expression of SLAMF6$^{var3}$, a gene editing agent (e.g. Cas9/gRNA RNP directed to exon 2) reducing the expression of SLAMF6$^{var1}$ and/or an exon-skipping oligonucleotide (e.g. directed to exon 2), reducing the expression of SLAMF6$^{var1}$.

Adoptive Cell Therapy

In another aspect, there is provided a T cell composition prepared as described herein, suitable for adoptive transfer into a recipient subject in need thereof. As used herein, and unless otherwise specified, the term "adoptive transfer" refers to a form of passive immunotherapy where previously sensitized immunologic agents (e.g., cells or serum) are transferred to the recipients. The phrases "adoptive transfer immunotherapy", "adoptive cell therapy" and "adoptive cell immunotherapy" are used interchangeably herein to denote a therapeutic or prophylactic regimen or modality, in which effector immunocompetent cells, such as the T cell compositions of the invention, are administered (adoptively transferred) to a subject in need thereof, to alleviate or ameliorate the development or symptoms of cancer or infectious diseases.

T lymphocytes (T cells) are one of a variety of distinct cell types involved in an immune response. The activity of T cells is regulated by antigen, presented to a T cell in the context of a major histocompatibility complex (MHC) molecule. The T cell receptor (TCR) then binds to the MHC-antigen complex. Once antigen is complexed to MHC, the MHC-antigen complex is bound by a specific TCR on a T cell, thereby altering the activity of that T cell. Proper activation of T lymphocytes by antigen-presenting cells requires stimulation not only of the TCR, but the combined and coordinated engagement of its co-receptors.

T helper cells (TH cells) assist other white blood cells in immunologic processes, including maturation of B cells into plasma cells and memory B cells, and activation of cytotoxic T cells and macrophages. These cells are also known as CD4$^+$ T cells because they express the CD4 glycoprotein on their surfaces. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response.

Cytotoxic T cells ($T_c$ cells, or CTLs) destroy virus-infected cells and tumor cells, and are also implicated in transplant rejection. These cells are also known as CD8$^+$ T cells since they express the CD8 glycoprotein at their surfaces. These cells recognize their targets by binding to antigen associated with MHC class I molecules, which are present on the surface of all nucleated cells.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress autoreactive T cells that escaped the process of negative selection in the thymus.

The TCR is a complex of integral membrane proteins, wherein stimulation by specific MHC-presented antigen recognition and binding by the clonotype-specific α/β heterodimer leads to activation of transcription and subsequent proliferation and effector functions (such as cytotoxic activity in CD8+ T cells and cytokine secretion in CD4+ T cells). This activation involves other subunits of the receptor complex as detailed below that couple the extracellular liganding event to downstream signaling pathways such as protein phosphorylation, the release of inositol phosphates and the elevation of intracellular calcium levels.

The intracellular portions of the CD3 γ, δ, ε, and ζ subunits contain copies of a sequence motif termed ITAMs (immunoreceptor tyrosine-based activation motifs). ITAMs can serve as protein tyrosine kinase substrates and, after phosphorylation, as binding sites for SH2 domains of yet other kinases. The regulation and mechanism of the recruitment of protein kinases to the activated T cell receptor involves members of both the Syk family (ZAP-70) and Src family (Lck) of kinases.

TCR stimulation as detailed above may be antigen-specific or antigen non-specific (Polyclonal). Suitable antigen-specific TCR activators include antigens bound to MHC molecules, typically in the context of antigen presenting cells (APC). Polyclonal TCR activators are capable of initiating the signal transduction and transcriptional activation pathways associated with specific TCR engagement in the absence of specific antigens. Suitable polyclonal T cell activators include antibodies that bind and crosslink the T cell receptor/CD3 complex, e.g. subunits as described herein. Exemplary antibodies that crosslink the T cell receptor include the HIT3a, UCHT1 and OKT3 monoclonal antibodies. The stimulation is provided at an amount and under conditions as known in the art so as to induce the above mentioned functional effects. Various non-limitative examples for TCR stimulation (both antigen-specific and polyclonal) are provided in the Examples herein below.

Typically, compositions for adoptive cell transfer are prepared by methods including activating a T cell population by a TCR stimulation, and expansion of the cells to obtain a therapeutically effective amount of effector T cells for administration. Such methods include but are not limited to, Rapid Expansion Protocols (REP).

In various embodiments, the TCR stimulation may be antigen non-specific (performed, for example, using antibodies specific to CD3 that activate the receptor upon binding, e.g. OKT3) or antigen-specific (using suitable antigen presenting cells and antigen). In the context of cancer treatment, antigen-specific stimulation typically employs stimulation to tumor-associated antigens. The term "tumor-associated antigen" (TAA) refers to any protein, peptide or antigen associated with (carried by, expressed by, produced by, secreted by, etc.) a tumor or tumor cell(s). Tumor-associated antigens may be (nearly) exclusively associated with a tumor or tumor cell(s) and not with healthy normal cells or may be over expressed (e.g., 2 times, 5 times, 10 times, 50 times, 100 times, 1000 times or more) in a tumor tissue or tumor cell(s) compared to healthy normal tissue or cells. More particularly, a TAA is an antigen capable of being presented (in processed form) by MHC determinants of the tumor cell. Hence, tumor-associated antigens are likely to be associated only with tumors or tumor cells expressing MHC molecules. Non-limitative examples of well-known TAA are MART-1, gp100$_{209-217}$, gp100$_{154-163}$, CSPG4, NY-ESO, MAGE-A1, Tyrosinase.

In some embodiments, one commonly used approach for stimulating proliferation, in particular of CD8+ T cells, is the incubation of T cells with soluble anti-CD3 antibody in the presence of Fc receptor-bearing accessory cells (feeder cells), an approach designated the REP. Antibody "presented" to T cells in this manner generates a more effective proliferative signal than soluble anti-CD3 alone or anti-CD3 immobilized on a plastic surface. In the treatment of cancer, adoptive cell therapy typically involves collecting T cells that are found within the tumor of the patient (referred to as tumor-infiltrating lymphocytes, TIL), which are encouraged to multiply ex vivo using high concentrations of IL-2, anti-CD3 and allo-reactive feeder cells. These T cells are then transferred back into the patient along with exogenous administration of IL-2 to further boost their anti-cancer activity.

Thus, according to certain additionally advantageous embodiments, activation and/or expansion is performed in the presence of feeder cells. The term "feeder cells" generally refers to cells of one type that are co-cultured with cells of a second type, to provide an environment in which the cells of the second type can be maintained and proliferated. For the purpose of the present invention, this term specifically refers to Fc receptor-bearing accessory cells, which are typically allo-reactive with the T cell containing population to be propagated. In other words, the feeder cells need not be histocompatible with the T-cell containing population to be propagated, and in certain advantageous embodiments the two populations typically HLA-mismatched. A typical example of feeder cells used in embodiments of the invention is allogeneic normal donor peripheral blood mononuclear cells, PBMC. Typically and advantageously, the use of such feeder cells is performed in conjunction with antigen non-specific TCR stimulation, e.g. by incubation with anti-gen non-specific stimulating antibodies, as detailed herein.

In another embodiment, adoptive transfer T cell compositions are prepared with irradiated PBMC (incapable of proliferation). For example, PBMC may conveniently be attenuated by irradiation by exposing the cells to 6000RAD. In another embodiment, adoptive transfer T cell compositions are prepared with artificial antigen presenting entities including antigen presenting cells and inert particles carrying antigens, to provide antigen-specific stimulation.

In various embodiments, T cell expansion may be performed for at least 5 and typically at least 6, 7, or 8 days. Typically, expansion is performed for up to about 16, 15, 14, 13, or 12 days, for example 5-15 days, e.g. 6-12 or more typically 8-15 days. In another embodiment, the population comprises CD8+ T cells. In another embodiment, the T cells are CD8+ T cells. In another embodiment, the cells are further genetically engineered or modified (e.g. to exert a desired antigen specificity). For example, in another embodiment, the cells are lymphocytes (e.g. purified T cells such as CTL) genetically engineered to express a TCR pre-designed to re-direct them against cancer cells or against pathogens (e.g. viruses). By means of a non-limitative example, T cells engineered to express a TCR directed against NY-ESO-1, an antigen expressed on many solid tumors, e.g. synovial sarcoma. In another embodiment, the cells are peripheral blood mononuclear cells genetically engineered to express a chimeric antigen receptor (CAR) to re-direct them against cancer cells or pathogens. For example, without limitation, CAR-T cells targeting CD19 may be used for the treatment of B cell malignancies such as acute lymphoblastic leukemia. In another embodiment, the cells are peripheral blood mononuclear cells genetically engineered to express genes that enhance their biological function. For example, without limitation, such genes may include membrane bound cytokine and cytokine receptor (e.g. IL-2 and IL-2R). In another embodiment the population comprises CD4$^+$ T cells. In another embodiment the population comprises a combination of CD8$^+$ T cells and CD4$^+$ T cells.

The cell composition may comprise a T cell-containing population in an effective amount. For example, an amount effective for adoptive transfer immunotherapy is an amount sufficient to induce or enhance a beneficial immune response such as an anti-tumor response, e.g. $10^6$ to $10^{12}$ cells. It is to be understood, that while cell preparations suitable for in vivo administration, particularly for human subjects, may contain pharmaceutically acceptable excipients or diluents, such preparations are sufficiently devoid of contamination by pathogens, toxins, pyrogens and any other biological and non-biological agents which are not recognized to be pharmaceutically acceptable. For example, without limitation, T cells for adoptive transfer immunotherapy may conveniently be suspended in an injection suitable buffer that contains sterile saline with 2% human albumin, and optionally IL-2 (e.g. 300 IU/ml).

According to certain preferable embodiments, the cell composition is histocompatible with the subject to be treated (e.g. autologous cells or MHC II-matched allogeneic cells).

The term "histocompatibility" refers to the similarity of tissue between different individuals. The level of histocompatibility describes how well matched the patient and donor are. The major histocompatibility determinants are the human leukocyte antigens (HLA). HLA typing is performed between the potential donor and the potential recipient to determine how close a HLA match the two are. The term "histocompatible" as used herein refers to embodiments in which all six of the HLA antigens (2 A antigens, 2 B antigens and 2 DR antigens) are the same between the donor and the recipient.

However, in other embodiments, donors and recipients who are "mismatched" at two or more antigens, for example 5 of 6, or in other embodiments, 4 of 6 or 3 of 6 match, may be encompassed by certain embodiments of the invention, despite the donor and recipient not having a complete match. The term "substantially histocompatible" as used herein refers to embodiments in which five out of six of the HLA antigens are the same between the donor and the recipient.

Cell Vaccines

According to some embodiments, the invention relates to the generation and use of improved tumor cell vaccines. Tumor cell lines for use in preparation of vaccines and immunogenic compositions may be obtained and prepared using well-known methods. Established tumor cell lines may be used, e.g. those disclosed in WO2012/156969, incorporated herein in its entirety, or may be raised from tumor biopsies. For example, cells can be obtained by disrupting biopsies by chemical (enzymatic) or physical methods (such as disruption or filtering). Cells can also be obtained from a cell suspension (fresh or cryopreserved cells).

According to the principles of the invention, the tumor cells are engineered as described herein. In various embodiments, the tumor cell population to be engineered or manipulated originally expresses SLAMF6 and/or variants thereof (e.g. SLAMF6$^{var1}$ or SLAMF6$^{var3}$). In other embodiments, said tumor cells lack substantial expression of SLAMF6 prior to manipulation. For example, tumor cells lacking substantial expression of SLAMF6 and/or variants thereof (e.g. solid tumors) may be engineered to express exogenous SLAMF6$^{var3}$, whereas tumor cells expressing SLAMF6 and/or variants thereof (e.g. hematopoietic tumors) may be engineered to selectively up-regulate SLAMF6$^{var3}$ expression and/or selectively down-regulate SLAMF6$^{var1}$ expression. In another particular embodiment, said tumor cells do not substantially express CD137.

One or more of the components of the media used for expanding cells may be changed, if they are found to improve the growth of cells. Typically, the purified tumor cells are irradiated or otherwise attenuated prior to vaccination. For example, the tumor cells can be washed and irradiated at 5,000-35,000 rads. For instance, for the preparation of an exemplary vaccine, cells may be irradiated (e.g. to 110 Gy or 170 Gy), conjugated with DNP, and prepared for subcutaneous administration at $10^6$-$10^9$, typically about $1$-$3*10^7$ tumor cells, optionally mixed with BCG or other adjuvants as known in the art. Without limitation, the finished product may contain e.g. 15-20 million irradiated DNP-modified melanoma cells suspended in a volume of 0.6 ml Hank's buffered salt solution (HBSS).

The purified tumor cells may be placed in a suitable medium, excipient, solution, or container for short term or long term storage. Said storage may require keeping the cells in a refrigerated or frozen environment. The tumor cells may be quickly frozen prior to storage in a frozen environment. The frozen sample may be contacted with a suitable cryopreservation medium or compound including but not limited to: dimethyl sulfoxide (DMSO), glycerol, ethylene glycol, sucrose, or glucose. A suitable medium, excipient, or solution may include but is not limited to: hanks salt solution, saline, cellular growth medium, or water. The medium, excipient, or solution may or may not be sterile.

The medium, excipient, or solution may contain preservative agents to maintain the sample in an adequate state for subsequent diagnostics or manipulation, or to prevent coagulation. Said preservatives may include citrate, ethylene diamine tetraacetic acid, sodium azide, or thimersol. The sample may be fixed prior to or during storage by any method known to the art such as using glutaraldehyde, formaldehyde, or methanol. The container may be any container suitable for storage and or transport of the biological sample including but not limited to: a cup, a cup with a lid, a tube, a sterile tube, a vacuum tube, a syringe, a bottle, a microscope slide, or any other suitable container. The container may or may not be sterile. In some cases, the sample may be stored in a commercial preparation suitable for storage of cells for subsequent cytological analysis such as but not limited to Cytyc ThinPrep, SurePath, or Monoprep.

In some embodiments, the purified irradiated tumor cells are stimulated with an adjuvant to increase immunogenicity. An adjuvant is an agent that may stimulate the immune system and increase the response to a vaccine, without having any specific antigenic effect in itself. An immunologic adjuvant is defined as any substance that acts to accelerate, prolong, or enhance antigen-specific immune responses when used in combination with specific vaccine antigens, and thus providing increased immunity to a particular disease. Adjuvants accomplish this task by mimicking specific sets of evolutionarily conserved molecules, so called PAMPs, which include liposomes, lipopolysaccharide (LPS), molecular cages for antigen, components of bacterial cell walls, and endocytosed nucleic acids such as double-stranded RNA (dsRNA), single-stranded DNA (ssDNA), and unmethylated CpG dinucleotide-containing DNA. Because immune systems have evolved to recognize these specific antigenic moieties, the presence of an adjuvant in conjunction with the vaccine can increase the innate immune response to the antigen by augmenting the activities of dendritic cells (DCs), lymphocytes, and macrophages by mimicking a natural infection. Furthermore, because adjuvants are attenuated beyond any function of virulence, they pose little or no independent threat to a host organism. In a particular embodiment, the cells are further stimulated with a SLAMF6$^{var3}$ ectodomain, as described herein and/or the composition further comprises an isolated soluble SLAMF6$^{var3}$ ectodomain.

In some embodiments, the tumor cell population used for generating the vaccine may be a hematopoietic tumor cell population (e.g. leukemia, lymphoma or myeloma populations). In other embodiments, said tumor cell population may be a solid tumor cell population. In other embodiments, said tumor cell population may be a carcinoma cell population. For example, without limitation, said tumor cell population may be a solid tumor cell population including but not limited to melanoma, pancreatic cancer, breast cancer, ovarian cancer, bladder cancer, liver cancer, lung cancer, prostate cancer, cervical cancer or colon cancer cells. In other exemplary embodiments, said tumor cell population may be a carcinoma cell population including but not limited to melanoma, ovarian carcinoma, pancreatic carcinoma, breast carcinoma, colon carcinoma or lung carcinoma cells. Each possibility represents a separate embodiment of the invention. In a particular embodiment, said tumor cell population is a melanoma cell population.

The compositions of the invention can be administered in a variety of ways. By way of non-limiting example, the composition may be delivered intravenously, or into a body cavity adjacent to the location of a solid tumor, such as the intraperitoneal cavity, or injected directly into or adjacent to a solid tumor. In certain embodiments, as a preferred route, tumor vaccine compositions of the present invention may be administered via subcutaneous or intradermal injections in proximity to the tumor, via intralymphatic or intravenous injection.

The pharmaceutical forms suitable for injection use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi. The carrier can be solvent or dispersion medium containing, for example, water, ethanol, polyol (for example, glycerol, propylene glycol, and liquid polyethylen glyol, and the like), suitable mixtures thereof, and vegetable oils. The proper fluidity can be maintained, for example, by the use of a coating, such as lecithin, by the maintenance of the required particle size in the case of dispersion and by the use of surfactants.

Dendritic cell vaccination is a form of immunotherapy designed to induce T cell-dependent immunity, such as cancer-specific T cell-dependent anti-tumor immunity, that can result in durable complete responses using DCs. A critical step in DC vaccination is the efficient presentation of disease-specific antigens to T cells. DCs are an essential component of vaccination through their capacity to capture, process, and present antigens to T cells. Activated (mature), antigen-loaded DCs initiate the differentiation of antigen-specific T cells into effector T cells that display unique functions and cytokine profiles. "DC maturation" further refers to the differentiation of DCs from an immature phenotype to a mature phenotype and is associated with a wide variety of cellular changes, including (1) decreased antigen-capture activity, (2) increased expression of surface MHC class II molecules and costimulatory molecules, (3) acquisition of chemokine receptors (e.g., CCR7), which guide their migration, and (4) the ability to secrete different cytokines (e.g., interleukin-12 [IL-12]) that control T cell differentiation. According to some embodiments, the cells are pulsed or loaded with antigens associated with the etiology and/or pathology of a disease to be treated.

The DC vaccines of the invention comprise in some embodiments a DC cell preparation of the invention, pulsed with at least one cancer-associated antigen, said vaccine further comprising a pharmaceutically acceptable carrier, excipient and/or adjuvant.

As used herein, the term "antigen-loaded" or "antigen pulsed" in the context of loading a DC with an antigen or antigens (e.g., tumor-associated antigens such as tumor cell lysate), means contacting the DC with the antigen(s) under conditions sufficient to allow the DC to take up (e.g., phagocytose) the antigen(s) and/or express the antigen(s) or peptides derived from the antigen(s) in the context of MHC molecules on the DC cell surface.

The expression "conditions sufficient to allow antigen phagocytosis and/or expression", as used herein, refers to the incubation of the dendritic cell in a suitable medium and for a sufficient time period to allow the capture of the immunogen and the processing and presentation of said immunogen to other cells of the immune system.

The cell populations and compositions can be formulated for administration in any convenient way for use in treatment of humans. For in vivo administration to humans, the cells and compositions disclosed herein can be formulated according to known methods used to prepare pharmaceutically useful compositions. The DCs can be combined in admixture, either as the sole active material or with other known active materials, (e.g., one or more chemotherapeutic agents) with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. In some embodiments, the cells are formulated for administration by a parenteral route. The term "parenteral" includes subcutaneous injections, intravenous, intramuscular, intra-cisternal injection, or infusion techniques. Also included are intra-tumoral injection, and direct intra-organ injection (e.g., intra-splenic or intra-hepatic injection). For injection or infusion techniques, the DCs may be suspended in any suitable injection buffer, such as, but not limited to, PBS or PBS containing anti-coagulants.

In another aspect there is provided a method for treating cancer in a human subject in need thereof, comprising administering to said subject a cell vaccine comprising a cell population engineered to selectively down-regulate SLAMF6$^{var1}$ expression.

Pharmaceutical Compositions

In other embodiments, the SLAMF6$^{var3}$ ectodomain and agonists thereof used in the methods of the invention are provided in the form of a pharmaceutical composition, optionally further comprising a pharmaceutically acceptable carrier, excipient or diluent.

Said compositions may be in any pharmaceutical form suitable for administration to a patient, including but not limited to solutions, suspensions, lyophilized powders for reconstitution with a suitable vehicle or dilution prior to usage, capsules, tablets, sustained-release formulations and the like. The compositions may comprise a therapeutically effective amount of an agent of the present invention, preferably in purified form, and a pharmaceutical excipient.

As used herein, "pharmaceutical excipient" includes solvents, dispersion media, coatings, antibacterial and antifungal agents, isotonic and absorption delaying agents etc. and combinations thereof, which are compatible with pharmaceutical administration. Hereinafter, the phrases "therapeutically acceptable carrier" and "pharmaceutically acceptable carrier", which may be used interchangeably, refer to a carrier or a diluent that does not cause significant irritation to an organism and does not abrogate the biological activity and properties of the administered compound. The compositions may also contain other active compounds providing supplemental, additional, or enhanced therapeutic functions. In another embodiment, the composition consists essentially of a SLAMF6$^{var3}$ ectodomain or agonist thereof and one or more pharmaceutical excipients. In another embodiment, the composition consists of a purified SLAMF6$^{var3}$ ectodomain (or agonist thereof) and one or more pharmaceutical excipients. Each possibility represents a separate embodiment of the invention.

In certain embodiments, the SLAMF6$^{var3}$ ectodomain further comprises an epitope tag (e.g. poly-histidine tag) and/or a plasma half-life elongating moiety. For example, the SLAMF6$^{var3}$ polypeptide may be fused or conjugated an immunoglobulin or a portion thereof. Other half-life elongating substances include biologically suitable polymers or copolymers, for example, a polyalkylene glycol compound, such as a polyethylene glycol or a polypropylene glycol. Other appropriate polyalkylene glycol compounds include, but are not limited to, charged or neutral polymers of the following types: dextran, polylysine, colominic acids or other carbohydrate based polymers, polymers of amino acids, and biotin derivatives.

Other examples of the half-life extending moiety, in accordance with the invention, include a copolymer of ethylene glycol, a copolymer of propylene glycol, a carboxymethylcellulose, a polyvinyl pyrrolidone, a poly-1,3-dioxolane, a poly-1,3,6-trioxane, an ethylene/maleic anhydride copolymer, a polyaminoacid (e.g., polylysine), a dextran n-vinyl pyrrolidone, a poly n-vinyl pyrrolidone, a propylene glycol homopolymer, a propylene oxide polymer, an ethylene oxide polymer, a polyoxyethylated polyol, a polyvinyl alcohol, a linear or branched glycosylated chain, a polyacetal, a long chain fatty acid, a long chain hydrophobic aliphatic group, an immunoglobulin light chain and heavy chain, an immunoglobulin Fc domain or a portion thereof (see, e.g., U.S. Pat. No. 6,660,843), a CH$_2$ domain of Fc, an albumin (e.g., human serum albumin (HSA)); see, e.g., U.S. Pat. No. 6,926,898 and US 2005/0054051; U.S. Pat. No. 6,887,470), a transthyretin (TTR; see, e.g., US 2003/0195154 A1; 2003/0191056 A1), or a thyroxine-binding globulin (TBG).

It should be understood, that the resulting polypeptide or conjugate is selected such that SLAMF6$^{var3}$ mediated activity is substantially maintained, as described herein.

In various other embodiments, the use of SLAMF6$^{var3}$ agonists, such as SLAMF6$^{var3}$-specific antibodies, is contemplated. The terms "antibody" or "antibodies" as used herein refer to an antibody, preferably a monoclonal antibody, or fragments thereof, including, but not limited to, a full length antibody having a human immunoglobulin constant region, a monoclonal IgG, a single chain antibody, a humanized monoclonal antibody, an F(ab')$_2$ fragment, an F(ab) fragment, an Fv fragment, a labeled antibody, an immobilized antibody and an antibody conjugated with a heterologous compound. Each possibility represents a separate embodiment of the invention. In one embodiment, the antibody is a monoclonal antibody. In another embodiment, the antibody is a polyclonal antibody. In another embodiment, the antibody is a humanized antibody.

Methods of generating monoclonal and polyclonal antibodies are well known in the art. Antibodies may be generated via any one of several known methods, which may employ induction of in vivo production of antibody molecules, screening of immunoglobulin libraries, or generation of monoclonal antibody molecules by continuous cell lines in culture. These include, but are not limited to, the hybridoma technique, the human B-cell hybridoma technique, and the Epstein-Barr virus (EBV)-hybridoma technique. Besides the conventional method of raising antibodies in vivo, antibodies can be generated in vitro using phage display technology, by methods well known in the art (e.g. Current Protocols in Immunology, Colligan et al (Eds.), John Wiley & Sons, Inc. (1992-2000), Chapter 17, Section 17.1).

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes. A pharmaceutical composition of the invention is formulated to be compatible with its intended route of administration. Methods to accomplish the administration are known to those of ordinary skill in the art. Examples of suitable excipients and modes for formulating the compositions are described in the latest edition of "Remington's Pharmaceutical Sciences" by E. W. Martin.

Pharmaceutical compositions according to the invention (e.g. containing SLAMF6$^{var3}$ ectodomain) are typically liquid formulations suitable for injection or infusion. Examples of administration of a pharmaceutical composition include oral ingestion, inhalation, intravenous and continues infusion, intraperitoneal, intramuscular, intracavity, subcutaneous, cutaneous, or transdermal administration. According to certain particular embodiments, the compositions are suitable for intralesional (e.g. intratumoral) administration. In other embodiments, the compositions are suitable for intravenous administration.

For example, saline solutions and aqueous dextrose and glycerol solutions can be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Solutions or suspensions used for intravenous administration typically include a carrier such as physiological saline, bacteriostatic water, Cremophor EL™ (BASF, Parsippany, N.J.), ethanol, or polyol. In all cases, the composition must be sterile and fluid for easy syringability. Proper fluidity can often be obtained using lecithin or surfactants. The composition must also be stable under the conditions of manufacture and storage. Prevention of microorganisms can be achieved with antibacterial and antifungal agents, e.g., parabens, chlorobutanol, phenol, ascorbic acid, thimerosal, etc. In many cases, isotonic agents (sugar), polyalcohols (mannitol and sorbitol), or sodium chloride may be included in the composition. Prolonged absorption of the composition can be accomplished by adding an agent which delays absorption, e.g., aluminum monostearate and gelatin. Where necessary, the composition may also include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Oral compositions include an inert diluent or edible carrier. The composition can be enclosed in gelatin or compressed into tablets. For the purpose of oral administration, the active agent can be incorporated with excipients and placed in tablets, troches, or capsules. Pharmaceutically compatible binding agents or adjuvant materials can be included in the composition. The tablets, troches, and capsules, may optionally contain a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; or a sweetening agent or a flavoring agent.

The composition may also be administered by a transmucosal or transdermal route. For example, antibodies that comprise an Fc portion may be capable of crossing mucous membranes in the intestine, mouth, or lungs (via Fc receptors). Transmucosal administration can be accomplished through the use of lozenges, nasal sprays, inhalers, or suppositories. Transdermal administration can also be accomplished through the use of a composition containing ointments, salves, gels, or creams known in the art. For transmucosal or transdermal administration, penetrants appropriate to the barrier to be permeated are used. For administration by inhalation, the antibodies are delivered in an aerosol spray from a pressured container or dispenser, which contains a propellant (e.g., liquid or gas) or a nebulizer. The composition can be formulated as a suppository, with traditional binders and carriers such as triglycerides.

Solutions or suspensions used for intradermal or subcutaneous application typically include at least one of the following components: a sterile diluent such as water, saline solution, fixed oils, polyethylene glycol, glycerin, propylene glycol, or other synthetic solvent; antibacterial agents such as benzyl alcohol or methyl parabens; antioxidants such as ascorbic acid or sodium bisulfite; chelating agents such as ethylenediaminetetraacetic acid (EDTA); buffers such as acetate, citrate, or phosphate; and tonicity agents such as sodium chloride or dextrose. The pH can be adjusted with acids or bases. Such preparations may be enclosed in ampoules, disposable syringes, or multiple dose vials.

In certain embodiments, polypeptide active agents (e.g. SLAMF6$^{var3}$ ectodomain) are prepared with carriers to protect the polypeptide against rapid elimination from the body. Biodegradable polymers (e.g., ethylene vinyl acetate, polyanhydrides, polyglycolic acid, collagen, polyorthoesters, and polylactic acid) are often used. Methods for the preparation of such formulations are known by those skilled in the art. Liposomal suspensions can be used as pharmaceutically acceptable carriers too. The liposomes can be prepared according to established methods known in the art (U.S. Pat. No. 4,522,811). In other particular embodiments, liposomes containing PEG moieties or glycolipids may advantageously be used to enhance blood plasma retention and/or to reduce liver uptake.

In some embodiments, larger liposomes (e.g. 300 nm or more) are used, which mediate uptake and clearance preferentially by the spleen and having reduced liver clearance. In other embodiments, smaller liposomes (e.g. 40 nm or less) are used, which preferentially mediate liver uptake and clearance. In yet other embodiments, liposomes of 40-300 nm are used, which may have enhanced blood plasma retention. In other embodiments, the liposomes may further contain polymers such as PEG. US 2011160642 discloses pegylated liposomal formulations having reduced accumulation in the liver and spleen. A range of liposomes formulated to evade uptake by the reticuloendothelial system and circulate for longer are described in U.S. Pat. No. 6,284,267.

In addition, the SLAMF6$^{var3}$ ectodomain or agonist of the present invention may be administered with various effector molecules such as heterologous polypeptides, drugs, radionucleotides, or toxins. Thus, in some embodiments, the SLAMF6$^{var3}$ ectodomain or agonist may be administered in combination (concurrent or sequential) with a cancer treatment, e.g. radiation or chemotherapy.

Continuous as well as intermittent intravenous administration can also be achieved using an implantable or external pump (e.g., INFUSAID pump). The use of such pumps and adjustment of dosing protocols to the required parameters are well within the abilities of the skilled artisan.

In another embodiment, administration or addition of the SLAMF6$^{var3}$ polypeptides or agonists of the invention may be performed in combination (concurrent or sequential) with administration of other immune modulators, e.g. signaling receptor-targeting reagents exhibiting a modifying effect on immune cell function. Examples for such reagents include e.g. antagonists or inhibitors (such as antibodies) of CTLA-4, PD-1 or PD-L1. Non-limitative examples for antibodies which are commercially available or under clinical investigation include CTLA-4 blocking antibody (YERVOY™, BMS, approved for use in the clinic at 1-3 mg/kg), PD-1 blocking antibodies (KEYTRUDA™, Merck, 0.5-2 mg/kg; OPDIVO™, BMS, 1-3 mg/kg), and PD-L1 targeting antibodies (ROCHE, under clinical investigation).

According to other aspects, the invention is directed to a kit containing a polypeptide comprising a SLAMF6$^{var3}$ ectodomain or an agonist thereof, and instructions to use the polypeptide in the methods of the invention.

In another embodiment the composition is not administered in the form of a vaccine further comprising an additional antigen. In another embodiment the composition is not administered by a therapeutic regimen adapted for vaccination. Vaccines and vaccination protocols are well known in the art. Vaccines typically contain one or more antigens to which a desired immune response is to be elicited (e.g. attenuated cancer cells or tumor associated antigens), and often contain additional adjuvants, used to boost or enhance the immune response (e.g. Alum or mineral oil).

An "effective amount" or "therapeutically effective amount" refers to an amount sufficient to exert a beneficial outcome in a method of the invention. More specifically, a therapeutically effective amount means an amount of active ingredients (e.g., SLAMF6$^{var3}$ ectodomain or cell composition) effective to prevent, alleviate, or ameliorate symptoms of a disorder (e.g., cancer) or prolong the survival of the subject being treated. Thus, an isolated SLAMF6$^{var3}$ ectodomain of the invention may be used in some embodiments in an amount effective to induce or enhance anti-tumor immunity a human subject in need thereof. As demonstrated herein, the compositions and methods of the invention provide for advantageously enhanced anti-tumor activity. Thus, in certain particular embodiments, an effective amount to be used in connection with compositions and methods of the invention may conveniently be reduced by up to 5%, 10%, 15%, 20% or up to 50% compared to hitherto known compositions and methods (e.g. administration of SLAMF6$^{var1}$ ectodomain).

Therapeutic Use In another aspect there is provided a method for treating cancer in a human subject in need thereof, comprising administering to the subject T cells engineered to express differentially SLAMF6$^{var3}$. In one embodiment, the T cells have been engineered to selectively up-regulate SLAMF6$^{var3}$ expression. In another embodiment, the T cells have been engineered to selectively down-regulate SLAMF6$^{var1}$ expression. In yet another embodiment, the T cells have been engineered to selectively up-regulate SLAMF6$^{var3}$ expression and to selectively down-regulate SLAMF6$^{var1}$ expression. In another embodiment said T cells are autologous. In another embodiment said T cells are allogeneic T cells histocompatible with said subject.

In another embodiment, the method comprises:
a) obtaining T cells form the subject, or from a donor histocompatible with the subject;
b) modulating the cells ex vivo to express differentially SLAMF6$^{var3}$; and
c) adoptively transferring the resulting T cells to said subject to thereby treat cancer in said subject.

In another embodiment, the T cells are further expanded and/or activated by incubation with an isolated SLAMF6$^{var3}$ ectodomain prior to administration to said subject.

In another aspect, the invention relates to T cells engineered to express differentially SLAMF6$^{var3}$, for use in treating cancer in a human subject in need thereof. In one embodiment, the T cells have been engineered to selectively up-regulate SLAMF6$^{var3}$ expression. Additionally or alternatively, the T cells have been engineered to selectively down-regulate SLAMF6$^{var1}$ expression. In various embodiments, said T cells are autologous, or are allogeneic T cells histocompatible with said subject. In another embodiment, said T cells have been generated by a method comprising ex vivo modulating T cells of the subject, or of a donor histocompatible with said subject, to express differentially SLAMF6$^{var3}$, and formulating the resulting T cells as an adoptive transfer composition for cancer treatment. In another embodiment, said T cells have been further expanded and/or activated by incubation with an isolated SLAMF6$^{var3}$ ectodomain (e.g. prior to formulation as an adoptive transfer composition for cancer treatment, or prior to adoptively transferring said composition to said subject).

In another aspect there is provided a method for treating cancer in a human subject in need thereof, comprising administering to said subject a cell vaccine comprising a cell population engineered to express differentially SLAMF6$^{var3}$. In one embodiment, the cell population is a tumor cell population, and the cell vaccine is a tumor cell vaccine. In a particular embodiment the tumor cell population is a melanoma cell population. In another embodiment the cell population is a dendritic cell (DC) and the cell vaccine is a DC vaccine. In another embodiment the cell population has been engineered to selectively up-regulate SLAMF6$^{var3}$ expression. In another embodiment, the T cells have been engineered to selectively down-regulate SLAMF6$^{var1}$ expression. In yet another embodiment, the T cells have been engineered to selectively up-regulate SLAMF6$^{var3}$ expression and to selectively down-regulate SLAMF6$^{var1}$ expression. In another embodiment the cell population has been engineered to express SLAMF6$^{var3}$ exogenously.

In another aspect the invention relates to a cell vaccine comprising a cell population engineered to express differentially SLAMF6$^{var3}$, for use in treating cancer in a human subject in need thereof In one embodiment, the cell population is a tumor cell population, and the cell vaccine is a tumor cell vaccine. In a particular embodiment the tumor cell population is a melanoma cell population. In another particular embodiment, the cell population is a dendritic cell (DC) population and the cell vaccine is a DC vaccine. In some embodiments, the cell population has been engineered to selectively up-regulate SLAMF6$^{var3}$ expression. Additionally or alternatively, the cell population has been engineered to selectively down-regulate SLAMF6$^{var1}$ expression. In other embodiments, the cell population has been engineered to express SLAMF6$^{var3}$ exogenously.

In another aspect, the invention provides a method for treating cancer in a human subject in need thereof, comprising administering to the subject, or contacting with T cells of said subject, an effective amount of an isolated human SLAMF6$^{var3}$ ectodomain, thereby treating cancer in said subject. In one embodiment, the method comprises administering to said subject an effective amount of an isolated human SLAMF6$^{var3}$ ectodomain. In another embodiment, the method comprises contacting T cells of said subject ex vivo with the isolated SLAMF6$^{var3}$ ectodomain in an amount effective to expand and/or activate said T cells, and adoptively transferring the resulting T cells to said subject to thereby treat cancer in said subject.

In another aspect, the invention relates to an isolated human SLAMF6$^{var3}$ ectodomain for use in treating cancer in a human subject in need thereof. In one embodiment, the isolated human SLAMF6$^{var3}$ ectodomain is for use by administration to said subject in an amount effective to treat cancer in said subject. In another embodiment the isolated human SLAMF6$^{var3}$ ectodomain is for use by contacting T cells of said subject ex vivo with said isolated human SLAMF6$^{var3}$ ectodomain in an amount effective to expand and/or activate said T cells, and adoptively transferring the resulting T cells to said subject to thereby treat cancer in said subject. In another embodiment, the isolated human SLAMF6$^{var3}$ ectodomain has been produced by a process comprising expressing a polypeptide precursor comprising an isolated human SLAMF6$^{var3}$ ectodomain fused to an N' SLAMF6$^{var1}$ signal peptide, in a mammalian expression system, and isolating the resulting ectodomain polypeptide. In a particular embodiment, the polypeptide precursor has the amino acid sequence as set forth in SEQ ID NO: 15.

Determination of a therapeutically effective amount (such as the amount effective to treat cancer in the subject) is well within the capability of those skilled in the art, especially in light of the detailed disclosure provided herein. Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition (See, e.g., Fingl, E. et al. (1975), "The Pharmacological Basis of Therapeutics," Ch. 1, p.1.).

For example, without limitation, a suitable dose range for administration of an isolated human SLAMF6$^{var3}$ ectodomain (e.g. generated by expression of the chimeric polypeptide precursor as disclosed herein) may be from 0.01-50 mg/kg, typically 0.05 mg/kg to 40 mg/kg, e.g. 0.1-20, 0.05-0.5, 0.1-1, 1-10, 2-20 or 1-40 mg/kg. Administration may be e.g. every 7 to 90 days, e.g. 7, 10, 14, 30, 60 or 90 days between doses. It is to be understood that the treatment may be maintained or adjusted by the treating physician to maintain clinical benefit and avoid limiting toxicities of the overall treatment program.

In some exemplary embodiments, an amount of an isolated human SLAMF6$^{var3}$ ectodomain effective to expand and/or activate T cells (e.g. T cell compositions for adoptive transfer therapy) may be e.g. 0.1-400 µg/ml, typically 1-200 µg/ml, e.g. 10-50, 2-100, or 50-200 µg/ml. For example, without limitation, T cell compositions for adoptive transfer treatment of cancer may be generated by a modified rapid expansion protocol comprising incubating tumor infiltrating lymphocytes (TIL) of the subject with irradiated PBMC (as feeder cells) at a ratio of TIL to PBMCs of 200:1 to 1:300, e.g. 1:200 to 1:100, in the presence of anti-CD3 antibodies at 1 ng/ml-1 µg/ml, preferably 10-100 ng/ml (e.g. 30 ng/ml of the OKT3 antibody), and 1-200 µg/ml, preferably 10-50 µg/ml of the isolated human SLAMF6$^{var3}$ ectodomain. Incubation may be for 5-15 days, typically 8-15 days.

In various embodiments, the compositions and methods of the invention may be used in the treatment of cancer in a human subject in need thereof, e.g. various malignancies including but not limited to the treatment or inhibition of non-solid cancers, e.g. hematopoietic malignancies such as all types of leukemia, e.g. acute lymphocytic leukemia (ALL), acute myelogenous leukemia (AML), chronic lymphocytic leukemia (CLL), chronic myelogenous leukemia (CML), myelodysplastic syndrome (MDS), mast cell leukemia, hairy cell leukemia, Hodgkin's disease, non-Hodgkin's lymphomas, Burkitt's lymphoma and multiple myeloma, as well as for the treatment or inhibition of solid tumors such as head and neck tumors, tumors in lip and oral cavity, pharynx, larynx, paranasal sinuses, major salivary glands, thyroid gland, esophagus, stomach, small intestine, colon, colorectum, anal canal, liver, gallbladder, extraliepatic bile ducts, ampulla of vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma. In certain particular embodiments, the cancer to be treated is selected from the group consisting of melanoma, pancreatic cancer, breast cancer, ovarian cancer, bladder cancer, liver cancer, lung cancer, prostate cancer, cervical cancer or colon cancer. In other embodiments, said cancer is selected from the group consisting of melanoma, ovarian carcinoma, pancreatic carcinoma, breast carcinoma, colon carcinoma or lung carcinoma cells. Each possibility represents a separate embodiment of the invention. In a particular embodiment, said cancer is melanoma.

In some embodiments, said cancer to be treated by the compositions and methods of the invention is characterized by surface expression of SLAMF6 and/or one or more variants thereof. For example, the cancer may be characterized by surface expression of SLAMF6$^{var1}$, SLAMF6$^{var2}$, SLAMF6$^{var3}$, SLAMF6$^{var4}$ or any combination thereof, wherein each possibility represents a separate embodiment of the invention. In other embodiments, Said cancer is characterized by lack of substantial (detectable) surface expression of SLAMF6 and/or one or more variants thereof. For example, the cancer may be characterized by lack of substantial surface expression of SLAMF6$^{var1}$, SLAMF6$^{var2}$, SLAMF6$^{var3}$, SLAMF6$^{var4}$ or any combination thereof, wherein each possibility represents a separate embodiment of the invention. For example, without limitation, when the cancer is characterized by surface expression of SLAMF6$^{var1}$, a cell vaccine (e.g. autologous cell vaccine) useful for the treatment of said cancer may include attenuated tumor cells of the subject that have been modulated ex vivo to reduce SLAMF6$^{var1}$ surface expression (and/or to induce SLAMF6$^{var3}$ expression). When the cancer is lack of substantial surface expression of SLAMF6$^{var1}$, said tumor cell vaccine may include a cell population modulated ex vivo to induce or enhance SLAMF6$^{var3}$ expression.

In another aspect the invention provides a therapeutic cell composition comprising a cell population engineered to express differentially SLAMF6$^{var3}$. In various embodiments, the composition is selected from the group consisting of: an adoptive transfer T cell composition, a tumor cell vaccine and a DC vaccine. In one embodiment the cell population is a human T cell population and the composition is an adoptive transfer T cell composition. In another embodiment the cell population is a human tumor cell population and the cell vaccine is a tumor cell vaccine. In a particular embodiment said tumor cell population is a melanoma cell population. In yet another embodiment the cell population is a human DC population and the cell vaccine is a DC vaccine. In another embodiment the cell population has been engineered to selectively up-regulate SLAMF6$^{var3}$ expression. In another embodiment, the T cells have been engineered to selectively down-regulate SLAMF6$^{var1}$ expression. In yet another embodiment, the T cells have been engineered to selectively up-regulate SLAMF6$^{var3}$ expression and to selectively down-regulate SLAMF6$^{var1}$ expression. In another embodiment the cell population has been engineered to express SLAMF6$^{var3}$ exogenously. In another aspect, there is provided a therapeutic cell composition comprising a cell population engineered to express differentially SLAMF6$^{var3}$ as described herein, for use in treating cancer in a human subject in need thereof.

In another aspect, there is provided a method of generating a therapeutic cell composition, comprising:
 a) obtaining a cell population selected from the group consisting of: T cells, tumor cells and DC; and
 b) modulating the cells ex vivo to express differentially SLAMF6$^{var3}$.

The following examples are presented in order to more fully illustrate some embodiments of the invention. They should, in no way be construed, however, as limiting the broad scope of the invention.

EXAMPLES

Materials and Methods
Detection of Splice Variants mRNA
mRNA was extracted from human peripheral blood mononuclear cells (PBMCs), Jurkat T cells, CD8$^+$ tumor-infiltrating lymphocytes (TILs) and SLAMF6-transfected melanoma cells. Reverse transcription polymerase chain reaction (RT-PCR) was performed with primers designed to produce PCR products with differing sizes for different SLAMF6 variants, as follows:

```
                                    (exon 1, SEQ ID NO: 2)
Forward primer - GCGGAAAGCATGTTGTGGCTG;

(exon 3, SEQ ID NO: 3)
Reverse primer - GGAGACAGTGAGGTTTGGCTG.
```

For quantitative RT-PCR, Jurkat cells (4×10⁶) were incubated in 24-well plates for 48 h at 37° C. in the presence of PMA (200 ng/ml) and ionomycin (300 ng/ml). Cells were collected and RNA was isolated using GenElute Mammalian Total RNA kit (Sigma, RTN70) according to the manufacturer's protocol. RNA was then transcribed to cDNA using qScript cDNA Synthesis kit (Quanta, 95047-100).

Real time PCR was performed using PerfeCT SYBR Green FastMIX ROX (Quanta, 95073-012). Primers used were:

```
SLAMF6^var1 + SLAMF6^var2 forward:
                                         (SEQ ID NO: 4)
CTGTTCCAATCGCTCCTGTT;

SLAMF6^var1 + SLAMF6^var2 reverse:
                                         (SEQ ID NO: 5)
GGGGTTAAGCTGCTTTGTGA;

SLAMF6^var4 forward:
                                         (SEQ ID NO: 6)
CTGTTCCAATCGCTCCTGTT;

SLAMF6^var4 reverse:
                                         (SEQ ID NO: 7)
CAGATGGAGCTCACAGGTCA;

SLAMF6^var3 forward:
                                         (SEQ ID NO: 8)
CTGTTCCAATCGCTCCTGTT;

SLAMF6^var3 reverse:
                                         (SEQ ID NO: 9)
CAGGGAGTAGGACTGGGTGA.
```

CRISPR-Cas9 Plasmid

For the generation of nucleic acid constructs for SLAMF6-specific CRISPR-Cas9 genome editing, the sequences specified in Table 1 below were cloned into the vector pSpCas9(BB)-2A-GFP (Addgene, Cambridge, MA), essentially as described (Wu et al. 2016, *ibid*). Construct 1 targets exon 2, and accordingly would affect only SLAMF6$^{var1}$, while construct 2 targets the signal peptide region, and accordingly would affect all three variants. Table 1 specifies the sequences of the transcribed single guide RNA (sgRNA) sequences.

TABLE 1

SgRNA sequences for gene editing

| SEQ ID NO: | Description | Sequence |
|---|---|---|
| 10 | Construct 1 (SLAMF6$^{var1}$-specific), single guide RNA, forward (SgRNA Fw) | CACCGAGAATCCCGTTCACCATCAA |
| 11 | Construct 1, SgRNA reverse (Rev) | AAACTTGATGGTGAACGGGATTCT |
| 12 | Construct 2 (variant non-specific), SgRNA Fw | CACCGAGAAGACAAACAGGAGCGATGTT |
| 13 | Construct 2, SgRNA Rev | AAACAACATCGCTCCTGTTTGTCTTCT |

Generation of SLAMF6 Knockout (KO) Jurkat Cells

Jurkat cells were washed twice in RPMI-/- and re-suspended in 10×10⁶ cells/ml RPMI. 5×10⁶ Jurkat cells with 5 μg SLAMF6-CRISPR plasmid were electroporated in Biorad 0.4 cm cuvettes using ECM 630 Electro Cell manipulator (BTX Harvard) at 260V, 975 μF, 1575 Ω. After electroporation cells were immediately seeded into complete RPMI medium. 48 h after transfection, cells expressing GFP were selected by sorting (ARIA-III Sorter). Cells lacking human SLAMF6 were selected by single cell sorting using the NT-7 antibody (Biolegend, specifically recognizing variants 1 and 2), and cultured for the establishment of colonies.

Aberrant SLAMF6 Expression on Melanoma Cells

PCDNA3.1+/C-(K)DYK plasmids encoding for different SLAMF6 variants were purchased from GenScript (clone i.d.: OHu04772, OHu04774, OHu04776 for SLAMF6$^{var1}$, SLAMF6$^{var3}$, and SLAMF6$^{var4}$, accession numbers NM_001184714.1, NM_001184715.1 and NM_001184716.1, respectively). Human melanoma cells were transfected using lipofectamine. G-418- resistant melanoma cells were sub-cloned and the stably transfected cells were used for experiments. For SLAMF6$^{var1}$ the cells were stained with anti-NTB-A antibody (NT-7, Biolegend) and sorted (ARIA-III). Positive cells were cultured and used for experiments.

Interferon Gamma (IFN-γ) Secretion

Tumor infiltrating lymphocytes (TILs, 1×10⁵) were co-cultured overnight at a 1:1 ratio with the indicated target melanoma cells. In another type of experiments, peripheral blood mononuclear cells were obtained from healthy donors and incubated for 3 days in the presence of seSLAMF6-var3 or IL-2. At the end of incubation cells were washed and activated overnight with 1 ug/ml plate bound anti CD3. In both experiments, conditioned medium was collected, and IFN-γ secretion was detected by ELISA (R&D) according to the manufacturer's protocol.

Intracellular Staining

TIL (1×10⁵) were co-cultured for 6 h, 37° C. at a 1:1 ratio with the indicated target melanoma cells. After 2 h, brefeldin A (eBioscience, 1 μg/ml) was added for 4 hours. After incubation, the cells were washed twice with PBS and stained with an anti-CD8 antibody (Biolegend). Following fixation and permeabilization (eBioscience protocol), intracellular IFN-γ and tumor necrosis factor alpha (TNF-α) were labeled with anti-IFN-γ and anti-TNF-α (Biolegend) for 30 min at RT. Cells were washed with permeabilization buffer, re-suspended in FACS buffer and subjected to flow cytometry.

Interleukin 2 (Il-2) Secretion

Wild-type (WT) Jurkat cells or single cell KO Jurkat cells (1×10⁵) were activated using phorbol 12-myristate 13-acetate (PMA, 200 ng/ml) and ionomycin (300 ng/ml) for 48 h at 37° C. Conditioned medium was collected and IL-2 secretion was detected using ELISA (R&D).

SLAMF6 Binding ELISA

MaxiSorb plates were pre-coated overnight with an Fc-fused ectodomain of SLAMF6$^{var1}$ (seSLAMF6_Fc, Creative Biomart, at 1 μg/ml and 4° C.). On the next day, the plate was washed and blocked using blocking buffer containing 1% BSA in PBSX1. Next, the plate was incubated for two hours with different concentrations of isolated ectodomains (containing 6-histidine tags) from SLAMF6$^{var1}$ (Prospec, seSLAMF6) or SLAMF6$^{var3}$ (Novoprotein/Bonopus, seSLAMF6-V3), or from SLAMF1, SLAMF7 or SLAMF8 (seSLAMF1, seSLAMF7 and seSLAMF8, respectively). The amount of receptor-bound ectodomain polypeptides was detected using horseradish peroxidase (HRP)- conjugated antibodies directed to the histidine tag (anti-HIS Abs) and quantified using an ELISA reader.

Cell Viability Assay

Pmel mouse splenocytes were activated for 7 days using 1 μg/ml gp100$_{(25-33)}$ peptide and 30 U/ml IL-2. Following expansion, the splenocytes were washed, counted and 1×10$^5$ cells were cultured in culture medium supplemented either with IL-2 or seSLAMF6$^{var3}$, or were alternatively left untreated ("No t"). After additional 4 days, the cells were harvested, washed and labeled with the Annexin V apoptosis detection kit. Viable cells (negative for both annexin V and propidium iodide, Annexin V$^-$/PI$^-$) were analyzed by flow cytometry.

Example 1. Aberrant Expression of SLAMF6 Variant 3 on Human Melanoma Cells Leads to Enhanced Anti-Melanoma T-Cell Activity In order to evaluate SLAMF6 interactions in trans (between adjacent cells), and since SLAMF6 is typically expressed only on hematopoietic cells, melanoma target cells aberrantly expressing SLAMF6 were generated. To this end, SLAMF6 variants were stably expressed in the melanoma line 526mel using pcDNA3.1+/C-(K)DYK plasmids (Genscript), as described above. mRNA expression of the different variants in the transfected melanoma cells is shown in FIG. 1.

Canonical SLAMF6 (var1) manifested a decreased capacity to stimulate cognate (A2$^+$) anti-melanoma TILs. In contradistinction, melanoma cells transfected with SLAMF6$^{var3}$ (526 mel-var3), unexpectedly demonstrated an increased capacity to stimulate anti-melanoma TILs, as determined by IFN-γ secretion (FIGS. 2A-B) and by an increased percentage of CD8$^+$ cells expressing IFN-γ and TNFα (FIGS. 3A-B). As can be further seen in FIGS. 2A-3B, melanoma cells transfected with SLAMF6$^{var4}$ did not manifest an increased capacity to stimulate anti-melanoma TILs under these experimental conditions.

Figure 2A:
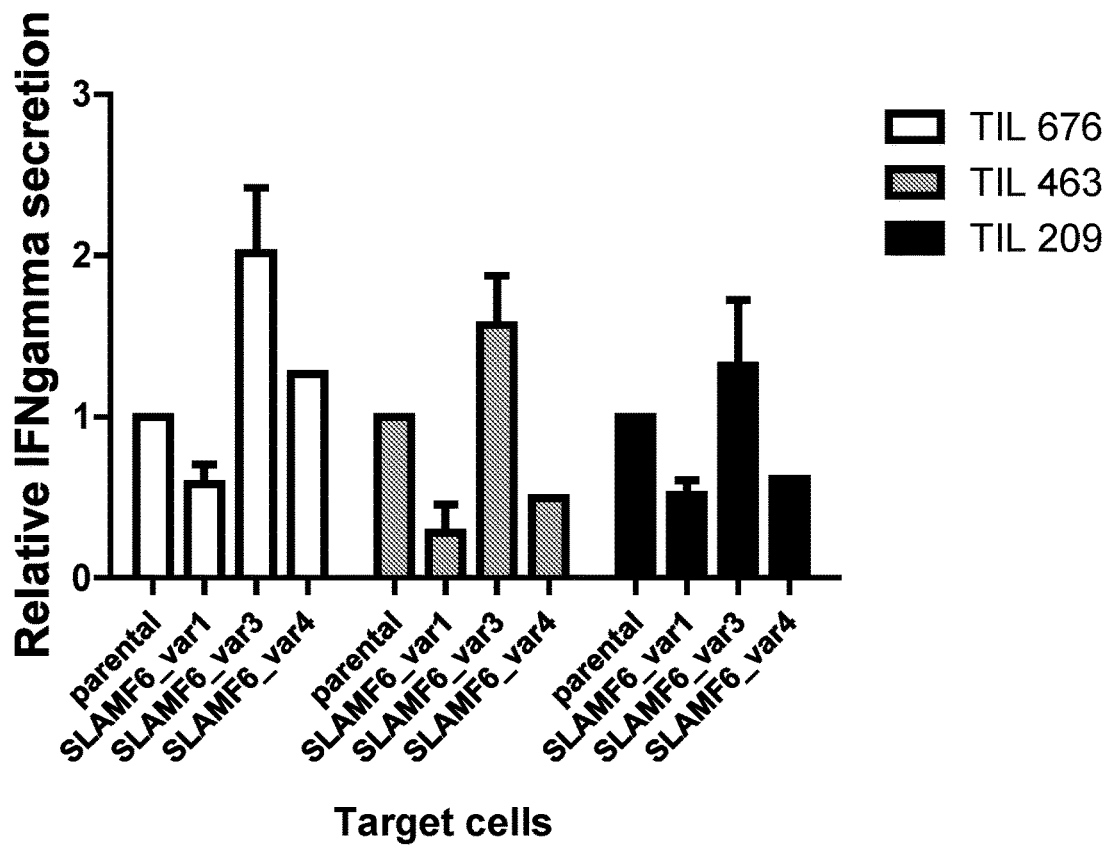
FIGS. 2A-2B. SLAMF6$^{var3}$ expression in target melanoma cells induces an increase in IFN-gamma secretion by TIL.
Figure 2B:
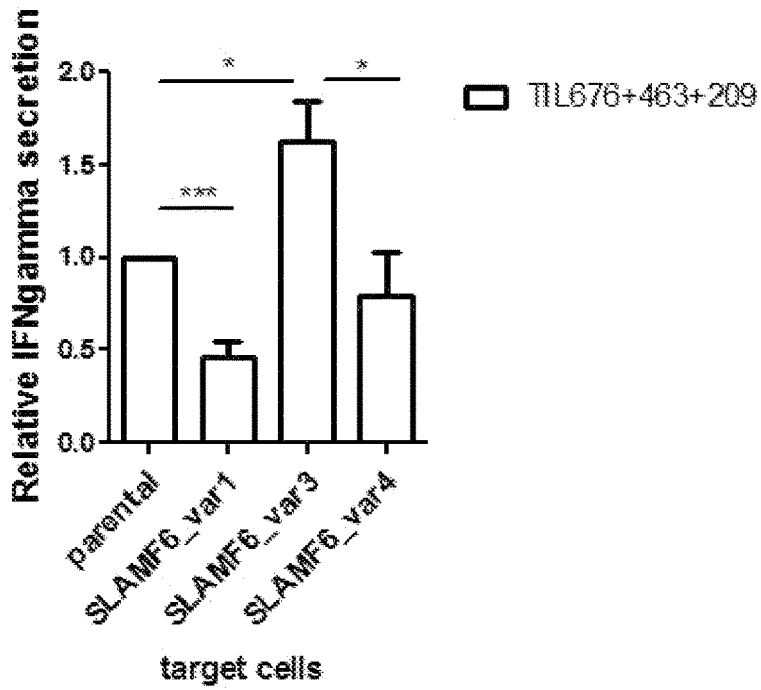
Figure 3A:
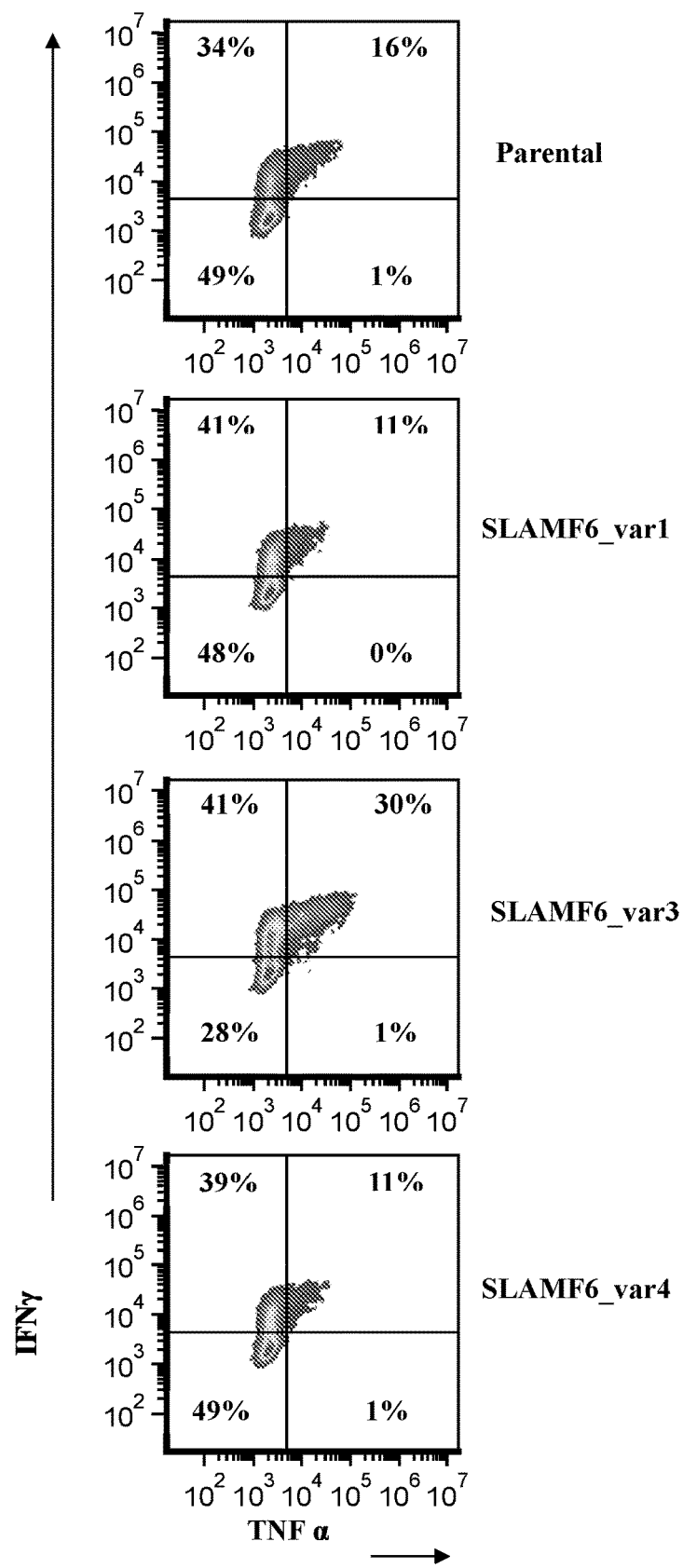
FIGS. 3A-3B. SLAMF6$^{var3}$ expression in target melanoma cells increases IFNγ$^+$TNFα$^{30}$ TILs.
Figure 3B:
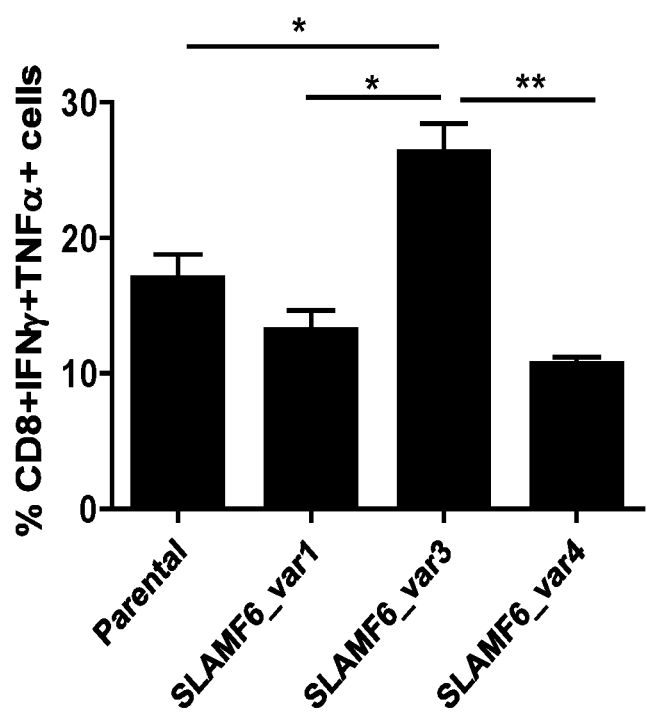

In the experiments described in FIG. 2A-B, SLAMF6-transfected melanoma cells of the mel526 line were co-cultured overnight with HLA-matched tumor infiltrating lymphocytes (TILs) from 3 melanoma patients (676, 463 and 209). IFN-γ in the culture medium was measured by ELISA. Values are relative to parental mel526. Each TIL was tested in two independent experiments (shown in FIG. 2A). Summary of the combined data from the three TILs in the two experiments is shown in FIG. 2B.

In the experiments described in FIG. 3A-B, TIL209 (1×10$^5$) were co-cultured for 6 h, 37° C. at a 1:1 ratio with the indicated target melanoma cells. After 2 h, brefeldin A was added. At the end of the incubation the cells were washed twice with PBS and stained with anti-CD8. Following fixation and permeabilization, intracellular IFN-γ and TNF-α were labeled. Cells were washed with permeabilization buffer, re-suspended in FACS buffer, and subjected to flow cytometry. FIG. 3A—dot plots, FIG. 3B—summary of triplicates showing percentage positive cells.

Thus, the results presented herein unexpectedly demonstrate that aberrant expression of SLAMF6$^{var3}$ on human melanoma cells leads to enhanced anti-melanoma human CD8$^+$ T-cell activity compared to non-transfected cells, while aberrant expression of other SLAMF6 variants did not result in such enhancement, or even resulted in reduced anti-melanoma activity.

Figure 4A:
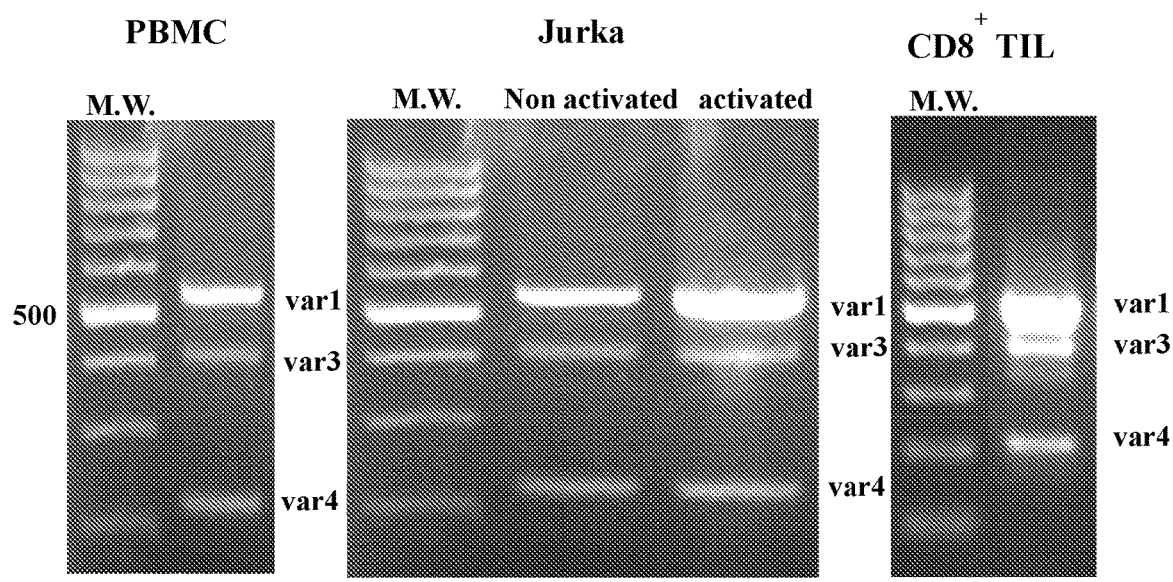
FIGS. 4A-4B. SLAMF6 variants are expressed in T cells.

Example 2. Expression of SLAMF6 Variants in T Cells and its Effects on the Level of T-Cell Response To further explore the role of SLAMF6 variants in lymphocytes, the expression of the different variants was assayed in resting and activated T cells by RT-PCR. As can be seen in FIG. 4A, mRNA of all tested variants was detected in various T cell populations, including Jurkat (CD4$^+$) T cells, anti-melanoma TILs (CD8$^+$), and PBMCs, with the level of var1 mRNA being the highest in all cells. As is further demonstrated in FIGS. 4A (middle panel, Jurkat cells) and 4B, the expression level of all variants was increased after T cell activation.

Figure 4B:
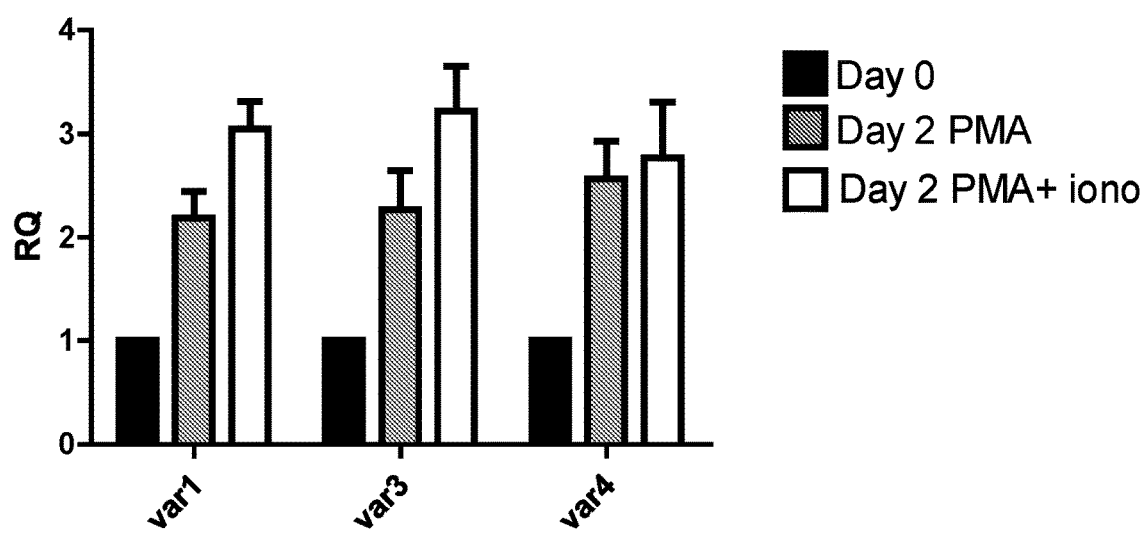

It is noted, that due to the similarity between SLAMF6$^{var1}$ and SLAMF6$^{var2}$, differing in one amino acid, the primers used to identify SLAMF6$^{var1}$ would also produce a PCR product having a similar size when SLAMF6$^{var2}$ is used as a template. Thus, in FIGS. 4A-B, var1 denotes mRNA corresponding to SLAMF6$^{var1}$ and SLAMF6$^{var2}$; var3 denotes mRNA corresponding to SLAMF6$^{var3}$, and var4 denotes mRNA corresponding to SLAMF6$^{var4}$.

Figure 5:
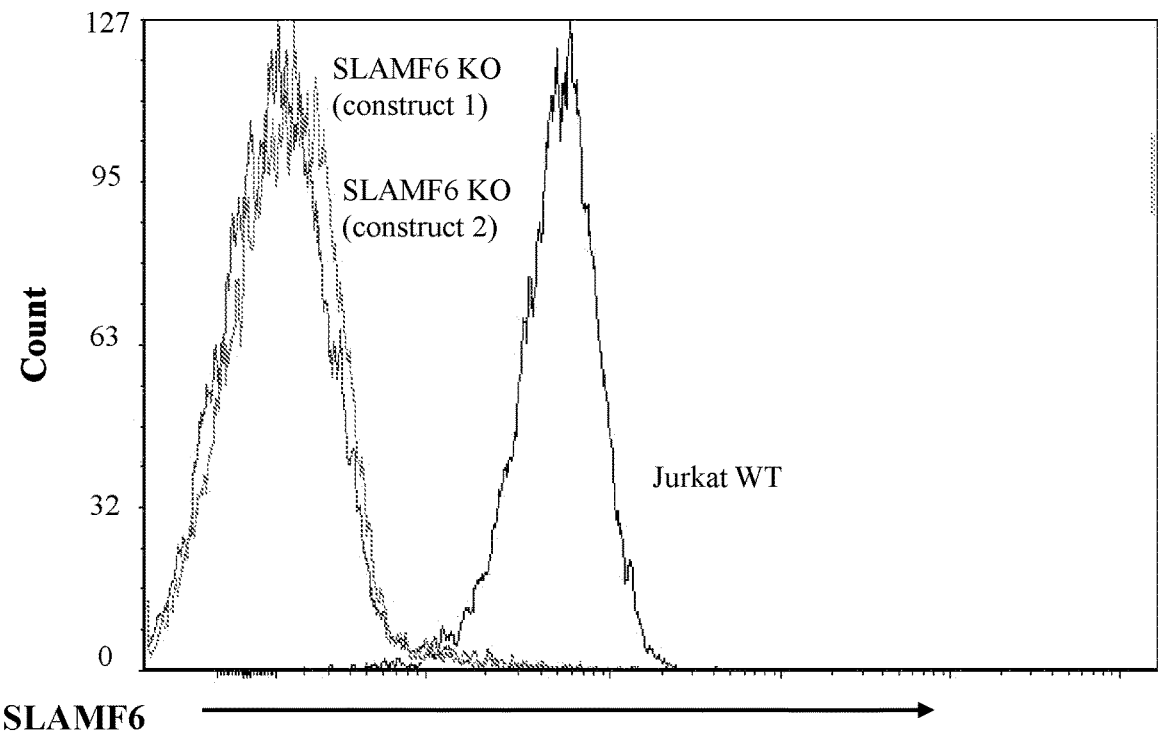
FIG. 5. Generation of SLAMF6 KO Jurkat cells. Jurkat cells lacking canonical SLAMF6 were produced by CRISPR-Cas9 genome editing. After transfection, cells lacking human canonical SLAMF6 were selected by single cell sorting, and cultured for the establishment of colonies.

Next, five single cell colonies of Jurkat cells were generated using two sgCRISPR-Cas9 constructs either targeting specifically SLAMF6$^{var1}$ (construct 1, also targeting SLAMF6$^{var2}$) or non-specifically targeting all SLAMF6 variants 1 to 4 (construct 2). After transfection, cells lacking surface expression of SLAMF6$^{var1}$ and SLAMF6$^{var2}$ were selected by single cell sorting, and cultured for the establishment of colonies. As can be seen in FIG. 5, both constructs yielded SLAMF6$^{var1}$-knockout colonies characterized by reduced SLAMF6 expression.

Figure 6:
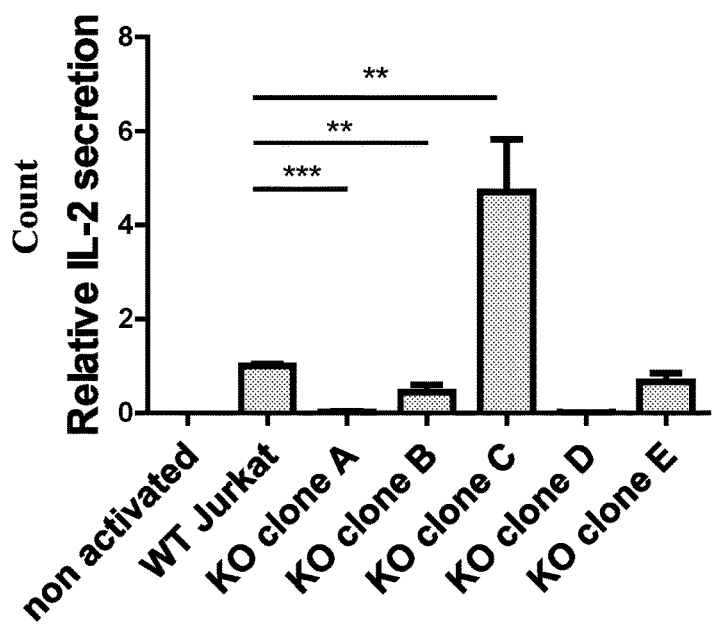
FIG. 6. Enhanced T cell activation of canonical (var1) SLAMF6-knockout (KO) Jurkat cells. Five single cell Jurkat clones were generated using sgCRISPR-Cas9 targeting SLAMF6. Cells were activated with PMA and ionomycin for 48 hours and IL-2 secretion was measured. Values are relative to WT. Summary of two experiments is shown. Two-tailed t test *p<0.05;  p<0.01; *p<0.001.

The resulting colonies were then tested functionally, for their response to activation stimuli (PMA and ionomycin). As can be seen in FIG. 6, lymphocytes from one of the colonies (clone C) showed an average 4.5-fold increase in IL-2 secretion in response to activation. As was further confirmed by RT-PCR, clone C, resulting from transfection by construct 1, is characterized by reduced SLAMF6$^{var1}$ mRNA levels without reduction of SLAMF6$^{var3}$ mRNA levels (resulting in an mRNA levels ratio of approximately 1:1 of the two variants).

In the remaining clones, including clones D and E, resulting from transfection by construct 2, and clones A and B, mRNA expression of additional SLAMF6 splice variants (SLAMF6$^{var3}$ and/or SLAMF6$^{var4}$) is further modulated. These clones either failed to manifest the enhanced activation response exhibited by clone C, or even showed a significant reduction in activation, as demonstrated in FIG. 6.

Figure 7:
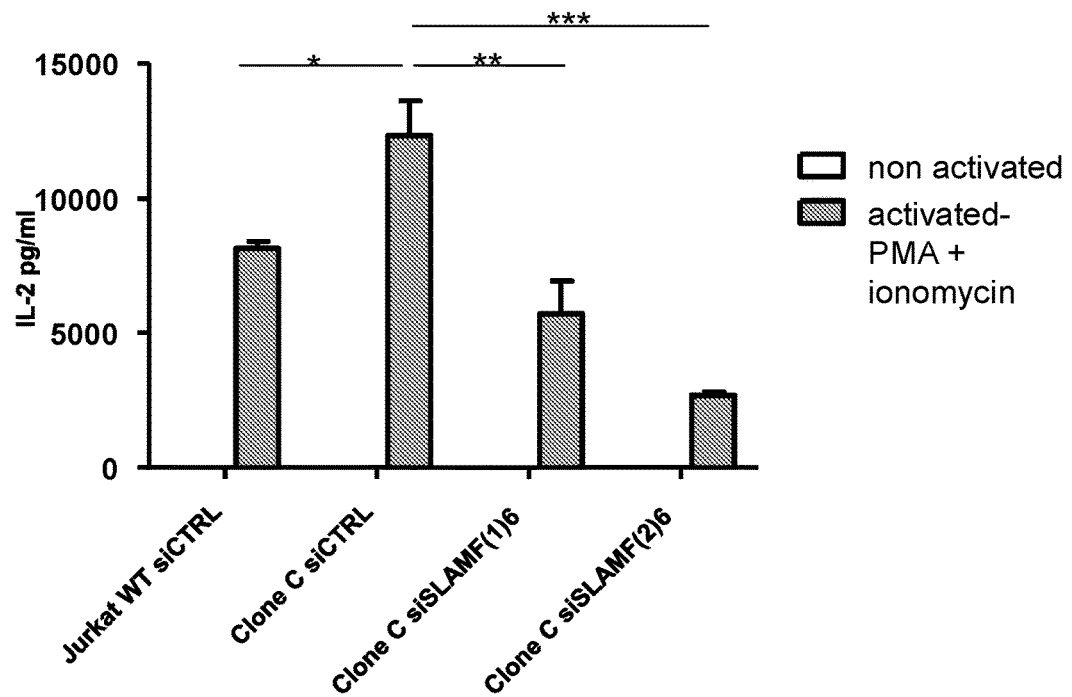
FIG. 7. Enhanced T cell activation of SLAMF6$^{var1}$ KO Jurkat cells is reversed upon silencing of remaining SLAMF6 variants. Jurkat WT Cells and Clone C cells were transfected with siRNA against SLAMF6 or siRNA control (QIAGEN) using electroporation. 24 h after electroporation the cells were activated with PMA and ionomycin for 48 hours and IL-2 secretion was measured. One way Annova test *p<0.05; p<0.01; *p<0.001.
Figure 8:
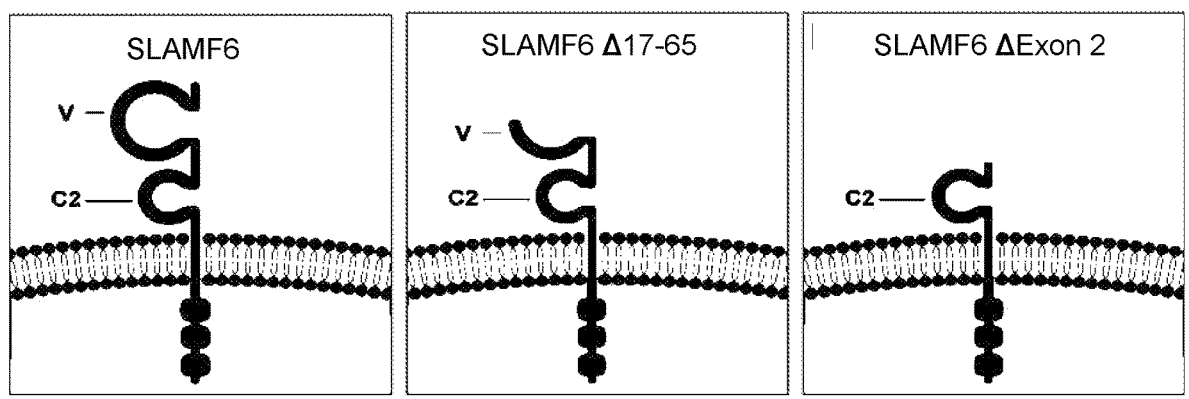
FIG. 8. Schematic representation of the SLAMF6 isoforms. Left panel—"SLAMF6"—canonical full length isoform (SLAMF6$^{var1}$). Extracellular domain, 22-226aa; Ig-like V-type domain, 35-120aa; Ig-like C-type domain, 132-209aa; transmembrane domain, 227-247aa; cytoplasmic domain, 248-331aa. Middle panel—"SLAMF6 Δ17-65"-3' spliced isoform (SLAMF6$^{var3}$); Right panel—"SLAM6 ΔExon2"- total exon 2 skipping isoform (SLAMF6$^{var4}$).
Figure 9A:
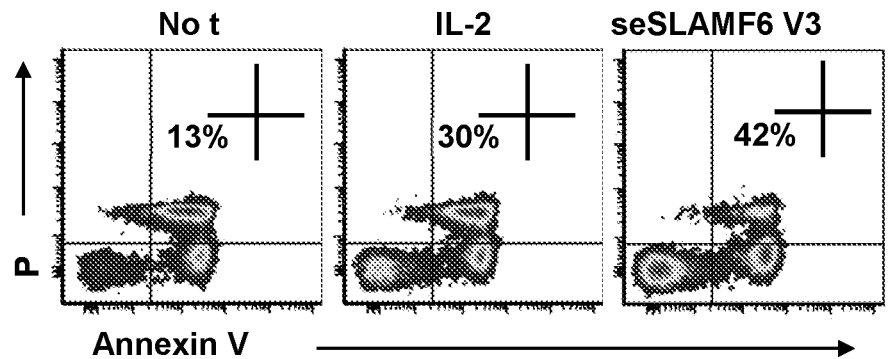
FIGS. 9A-9B. A soluble ectodomain of SLAMF6$^{var3}$ (seSLAMF6-V3) prevents T cell activation-induced cell death (AICD).
Figure 9B:
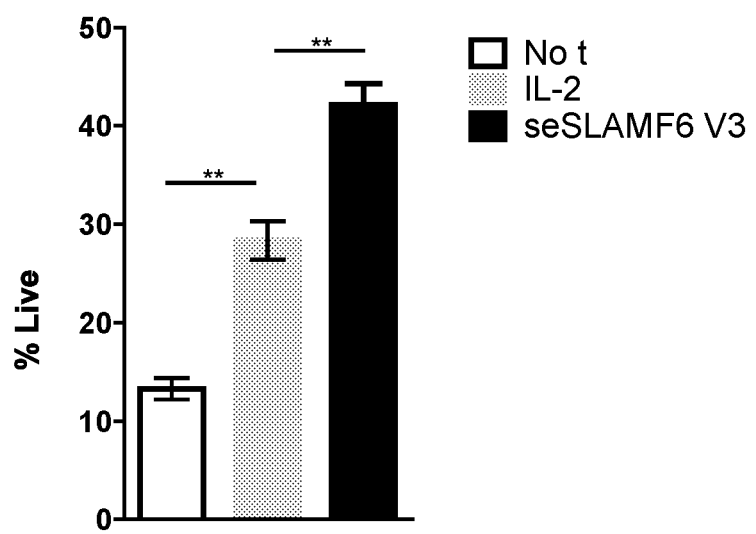
Figure 10:
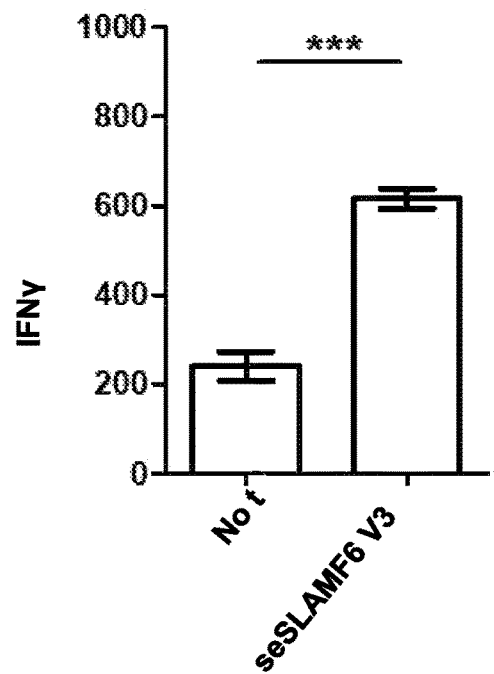
FIG. 10. T cell co-stimulation. Human PBMCs were incubated for 3 days with seSLAMF6-V3 followed by an overnight activation with anti CD3 antibodies. IFN-γ secretion to the medium was measured by ELISA. Two-tailed t test ***p<0.001.
Figure 11:
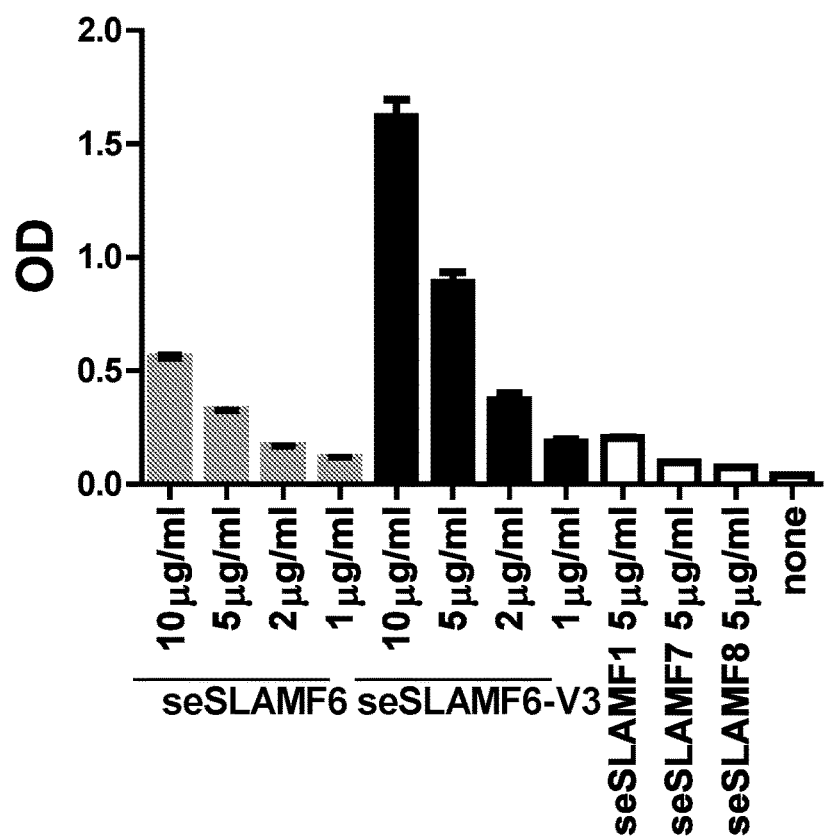
FIG. 11. seSLAMF6-V3 binding to full length seSLAMF6-Fc using ELISA. seSLAMF6-Fc was pre-coated to MaxiSorb plate. Soluble ectodomains from various SLAM family members (seSLAMF6, seSLAMF6-V3, seSLAMF1, seSLAMF7 and seSLAMF8, all containing 6-Histidine tags) were then added. An anti- Histidine antibody was used for detection.

The specificity of these finding was further confirmed using SLAMF6-specific gene silencing. To this end, Jurkat cells (wild type and clone C knockout cells) were transfected with siRNA against SLAMF6 or siRNA control (QIAGEN) using electroporation (250V, 300 μF, 10000 Ω, ECM 630 electro cell manipulator BTX HARVARD APPARATUS). The siRNA sequence is from the non coding region 3' to the gene and therefore silences all variants of SLAMF6. 24 h after electroporation the cells were activated with PMA and ionomycin for 48 hours and IL-2 secretion was measured. One way Annova test *p<0.05; p<0.01; *p<0.001. As can be seen in FIG. 7, the enhanced response to activation stimuli observed in clone C was completely reversed when cells were treated with anti-SLAMF6 siRNA.

Thus, the level of expression of different SLAMF6 variants affects the level of T-cell response and activation. Specific down-regulation of SLAMF6$^{var1}$ in the absence of SLAMF6$^{var3}$ down-regulation results in increased T cell activation, while non-specific down-regulation of SLAMF6 variants does not lead to such enhancement, and may be associated with reduced T cell activation.

Example 3. Synthesis of an Isolated SLAMF6$^{var3}$ Ectodomain

The following sequence was cloned into an expression plasmid (Novoprotein/BonOpus) and expressed recombinantly in mammalian cell lines:

Nucleic acid sequence:

(SEQ ID NO: 19)

ATGTTGTGGCTGTTCCAATCGCTCCTGTTTGTCTTCTGCTTTGGCCCAGG

GAATGTAGTTTCAGTACCCCATGAAACCAAAAGTCCAGAAATCCACGTGA

CTAATCCGAAACAGGGAAAGCGACTGAACTTCACCCAGTCCTACTCCCTG

CAACTCAGCAACCTGAAGATGGAAGACACAGGCTCTTACAGAGCCCAGAT

ATCCACAAAGACCTCTGCAAAGCTGTCCAGTTACACTCTGAGGATATTAA

GACAACTGAGGAACATACAAGTTACCAATCACAGTCAGCTATTTCAGAAT

ATGACCTGTGAGCTCCATCTGACTTGCTCTGTGGAGGATGCAGATGACAA

TGTCTCATTCAGATGGGAGGCCTTGGGAAACACACTTTCAAGTCAGCCAA

ACCTCACTGTCTCCTGGGACCCCAGGATTTCCAGTGAACAGGACTACACC

TGCATAGCAGAGAATGCTGTCAGTAATTTATCCTTCTCTGTCTCTGCCCA

GAAGCTTTGCGAAGATGTTAAAATTCAATATACAGATACCAAAATGGGAT

CTCACCACCACCACCACCACTGA;

Amino acid sequence:

(SEQ ID NO: 15)

MLWLFQSLLFVFCFGPGNVVSVPHETKSPEIHVTNPKQGKRLNFTQSYSL

QLSNLKMEDTGSYRAQISTKTSAKLSSYTLRILRQLRNIQVTNHSQLFQN

MTCELHLTCSVEDADDNVSFRWEALGNTLSSQPNLTVSWDPRISSEQDYT

CIAENAVSNLSFSVSAQKLCEDVKIQYTDTKMGSHHHHHH.

The sequence includes an N' signal peptide (bold) and a C' 6-histidine tag. The polypeptide was expressed in HEK293 cells, wherein secretive expression was observed in cells harvested after five days of transfection. The resulting SLAMF6$^{var3}$ ectodomain polypeptide was purified by a chelating SFF(Ni) column.

Since the SLAMF6$^{var3}$ ectodomain precursor denoted by SEQ ID NO: 15 is a chimeric polypeptide, comprising a heterologous signal peptide (namely the signal peptide of SLAMF6$^{var1}$, differing from that of SLAMF6$^{var3}$ by further inclusion of the underlined penta-peptide sequence) fused to the SLAMF6$^{var3}$ ectodomain sequence, the mature, processed recombinant SLAMF6$^{var3}$ ectodomain polypeptide that was produced and isolated was further characterized by mass spectrometry. It was found that the mature SLAMF6$^{var3}$ as isolated in this system retained part of the signal peptide, comprising at least the penta-peptide GNVVS (SEQ ID NO: 20), and up to 11 amino acids of the heterologous signal peptide sequence. Thus, sequences derived from amino acids 10-21 of SEQ ID NO: 15 were retained at least in part in the isolated ectodomain preparation. This isolated SLAMF6$^{var3}$ ectodomain, herein designated "seSLAMF6$^{var3}$", was further characterized as a therapeutic agent, as detailed hereinbelow.

Example 4. seSLAMF6$^{var3}$ prevents T Cell Activation-Induced Cell Death (AICD) and acts to Co-Stimulate Activated T Cells The functional properties of the isolated seSLAMF6$^{var3}$ polypeptides were then determined. To this end, the ectodomain polypeptide as described in Example 3 (designated throughout the Examples and Figures as seSLAMF6$^{var3}$ or seSLAMF6-V3), was incubated in vitro with murine splenocytes in a system designed to measure long-term T cell activation and secondary apoptosis (activation-induced cell death, AICD). As can be seen in FIGS. 9A and 9B, seSLAMF6$^{var3}$ significantly reduced AICD and improved T cell survival following one week of intense activation. Similar results were obtained for human T cells, in experiments performed using human PBMC. As can be further seen in FIGS. 9A-9B, the effect of seSLAMF6$^{var3}$ on prevention of AICD in murine splenocytes was significantly more pronounced compared to that of IL-2.

Next, the ability of seSLAMF6$^{var3}$ to provide T cell co-stimulation was assayed in a 3-day activation protocol. To this end, human peripheral blood mononuclear cells (PBMC) were incubated for 3 days with seSLAMF6$^{var3}$ followed by an overnight activation on plates pre-coated by anti CD3 antibodies (1 μg/ml in PBS for 1 hr). As can be seen in FIG. 10, T cells co-stimulated by seSLAMF6$^{var3}$ secreted increased levels of interferon-gamma (IFN-γ) following activation compared to T cells that did not receive seSLAMF6$^{var3}$ at the pre-activation phase- "No t".

Finally, seSLAMF6$^{var3}$ binding to the SLAMF6$^{var1}$ ectodomain (Fc-conjugated, seSLAMF6-Fc) was validated using ELISA (FIG. 11). As can be seen in FIG. 11, seSLAMF6$^{var3}$ was capable of binding seSLAMF6-Fc in a dose-dependent manner, whether other members of the SLAM family were not. In addition, it was surprisingly demonstrated that seSLAMF6$^{var3}$ bound to seSLAMF6-Fc with a greater affinity than the homotypic binding identified for the isolated SLAMF6$^{var1}$ ectodomain (seSLAMF6).

The invention claimed is:

1. A therapeutic cell composition comprising a cell population engineered to express preferentially SLAMF6$^{var3}$.

2. The composition of claim 1, selected from the group consisting of: an adoptive transfer T cell composition, a tumor cell vaccine, and a dendritic cell (DC) vaccine.

3. The composition of claim 2, wherein the cell population is a human T cell population.

4. The composition of claim 2, wherein the cell population is a human melanoma cell population and the cell vaccine is a tumor cell vaccine.

5. The composition of claim 2, wherein the cell population has been engineered to selectively down-regulate SLAMF6$^{var1}$ expression.

6. The composition of claim 2, wherein the cell population has been engineered to selectively up-regulate SLAMF6$^{var3}$ expression.

7. The composition of claim 2, wherein the cell population has been engineered to express SLAMF6$^{var3}$ exogenously.

8. A method for treating cancer in a human subject in need thereof, comprising administering to the subject T cells engineered to express preferentially SLAMF6$^{var3}$, or a cell vaccine comprising a cell population engineered to express preferentially SLAMF6$^{var3}$.

9. The method of claim 8, wherein the T cells have been engineered to selectively up-regulate SLAMF6$^{var3}$ expression and/or to selectively down-regulate SLAMF6$^{var1}$ expression.

10. The method of claim 8, comprising administering to the subject T cells engineered to express preferentially SLAMF6$^{var3}$.

11. The method of claim 10, wherein said T cells are autologous, or wherein said T cells are allogeneic T cells histocompatible with said subject.

12. The method of claim 10, comprising:
a) obtaining T cells form the subject, or from a donor histocompatible with the subject;
b) modulating the cells ex vivo to express preferentially SLAMF6$^{var3}$; and
c) adoptively transferring the resulting T cells to said subject to thereby treat cancer in said subject.

13. The method of claim 12, wherein the T cells are further expanded and/or activated by incubation with an isolated SLAMF6$^{var3}$ ectodomain prior to administration to said subject.

14. The method of claim 8, comprising administering to said subject a cell vaccine comprising a cell population engineered to express preferentially SLAMF6$^{var3}$.

15. The method of claim 14, wherein the cell population is a tumor cell population, and the cell vaccine is a tumor cell vaccine, or wherein the cell population is a DC population and the cell vaccine is a DC vaccine.

16. The method of claim 15, wherein the tumor cell population is a melanoma cell population.

17. The method of claim 14, wherein the cell population has been engineered to express SLAMF6$^{var3}$ exogenously.

18. A method of generating a therapeutic cell composition, comprising:
a) obtaining a cell population selected from the group consisting of: T cells, tumor cells, and DC; and
b) modulating the cells ex vivo to express preferentially SLAMF6$^{var3}$.

19. A method for treating cancer in a human subject in need thereof, comprising administering to the subject, or contacting with T cells of said subject, an effective amount of an isolated human SLAMF6$^{var3}$ ectodomain, thereby treating cancer in said subject.

20. The method of claim 19, comprising administering to said subject an effective amount of an isolated human SLAMF6$^{var3}$ ectodomain.

21. The method of claim 19, comprising contacting T cells of said subject ex vivo with the isolated SLAMF6$^{var3}$ ectodomain in an amount effective to expand and/or activate said T cells, and adoptively transferring the resulting T cells to said subject to thereby treat cancer in said subject.

22. A chimeric polypeptide precursor comprising an isolated human SLAMF6$^{var3}$ ectodomain fused to an N' SLAMF6$^{var1}$ signal peptide.

23. The polypeptide precursor of claim 22, having the amino acid sequence as set forth in SEQ ID NO: 15, and/or encoded by a polynucleotide as set forth in SEQ ID NO: 19.

24. A polynucleotide encoding the polypeptide precursor of claim 23.

25. An isolated human SLAMF6$^{var3}$ ectodomain produced by a process comprising expressing the polypeptide precursor of claim 22 in a mammalian expression system and isolating the resulting ectodomain polypeptide.

* * * * *